United States Patent
Kim et al.

(10) Patent No.: US 10,918,736 B2
(45) Date of Patent: Feb. 16, 2021

(54) CONJUGATE OF THERAPEUTIC ENZYMES

(71) Applicant: HANMI PHARM. CO., LTD., Hwaseong-si (KR)

(72) Inventors: Dae Jin Kim, Hwaseong-si (KR); Jung Kuk Kim, Hwaseong-si (KR); Sung Youb Jung, Hwaseong-si (KR); Se Chang Kwon, Hwaseong-si (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 58 days.

(21) Appl. No.: 16/073,598

(22) PCT Filed: Jan. 31, 2017

(86) PCT No.: PCT/KR2017/001016
§ 371 (c)(1),
(2) Date: Jul. 27, 2018

(87) PCT Pub. No.: WO2017/131496
PCT Pub. Date: Aug. 3, 2017

(65) Prior Publication Data
US 2019/0046657 A1    Feb. 14, 2019

(30) Foreign Application Priority Data
Jan. 29, 2016 (KR) .................. 10-2016-0011886

(51) Int. Cl.
| | | |
|---|---|---|
| A61K 47/68 | (2017.01) | |
| C12N 9/96 | (2006.01) | |
| C12N 9/40 | (2006.01) | |
| C12N 9/16 | (2006.01) | |
| C08G 65/328 | (2006.01) | |
| C12N 9/24 | (2006.01) | |
| C08G 65/333 | (2006.01) | |
| A61K 38/00 | (2006.01) | |

(52) U.S. Cl.
CPC .......... *A61K 47/6815* (2017.08); *A61K 47/68* (2017.08); *C08G 65/328* (2013.01); *C08G 65/33396* (2013.01); *C12N 9/16* (2013.01); *C12N 9/2402* (2013.01); *C12N 9/2405* (2013.01); *C12N 9/2465* (2013.01); *C12N 9/96* (2013.01); *A61K 38/00* (2013.01); *C07K 2319/30* (2013.01); *C12Y 302/01022* (2013.01)

(58) Field of Classification Search
CPC combination set(s) only.
See application file for complete search history.

(56) References Cited

U.S. PATENT DOCUMENTS 8,124,094 B2 *  2/2012  Kim ................... A61K 47/6811
                                                         424/178.1

FOREIGN PATENT DOCUMENTS

| CN | 1723220 A | 1/2006 |
|---|---|---|
| CN | 104039831 A | 9/2014 |
| JP | 2007-536211 | 12/2007 |
| JP | 2013-508367 | 3/2013 |
| JP | 2014-517808 | 7/2014 |
| KR | 10-2002-0010363 A | 2/2002 |
| KR | 10-0754667 B1 | 9/2007 |
| KR | 10-2014-0037961 A | 3/2014 |
| KR | 10-2015-0008011 A | 1/2015 |
| RU | 2356909 C2 | 5/2009 |
| WO | 96-32478 A1 | 10/1996 |
| WO | 97-34631 A1 | 9/1997 |
| WO | 2005/047334 A1 | 5/2005 |
| WO | 2013/100702 A1 | 7/2013 |
| WO | 2014/193173 A1 | 12/2014 |
| WO | 2015/009052 A1 | 1/2015 |
| WO | 2015/060722 | 4/2015 |

OTHER PUBLICATIONS

Beck, M. Human Genetics 2007 vol. 121, pp. 1-21.*
James E. Stefano et al., "In vitro and in vivo evaluation of a non-carbohydrate targeting platform for lysosomal proteins", Journal of Controlled Release, Apr. 17, 2009, vol. 135, pp. 113-118 (total 6 pages).
European Patent Office; Communication dated Sep. 19, 2019 issued in counterpart application No. 17744617.6.
Michael Beck, "New therapeutic options for lysosomal storage disorder: enzyme replacement, small molecules and gene therapy", Human Genetics, 2007, pp. 1-22, vol. 121, No. 1.
Frances M. Platt, et al., "Lysosomal storage disorders: The cellular impact of lysosomal dysfunction" Journal of Cell Biology, 2012, pp. 723-734, vol. 199, No. 5.
International Search Report for PCT/KR2017/001016 dated May 10, 2017 [PCT/ISA/210].

* cited by examiner

*Primary Examiner* — Heidi Reese
(74) *Attorney, Agent, or Firm* — Sughrue Mion, PLLC

(57) ABSTRACT

The present invention relates to a conjugate in which an immunoglobulin Fc region is linked to therapeutic enzymes through a non-peptide polymer linkage moiety, and more specifically, to a conjugate in which a non-peptide polymer linkage moiety is specifically linked to an immunoglobulin Fc, a method of preparing the same, and a composition comprising the same.

25 Claims, 6 Drawing Sheets

[FIG. 1]
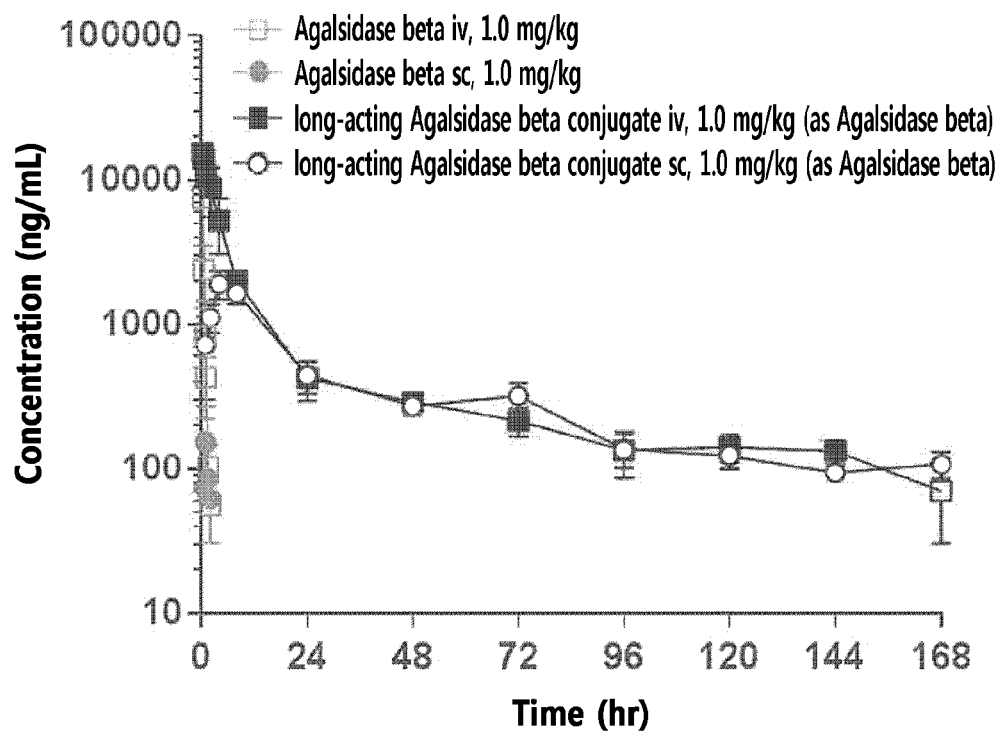

[FIG. 2]
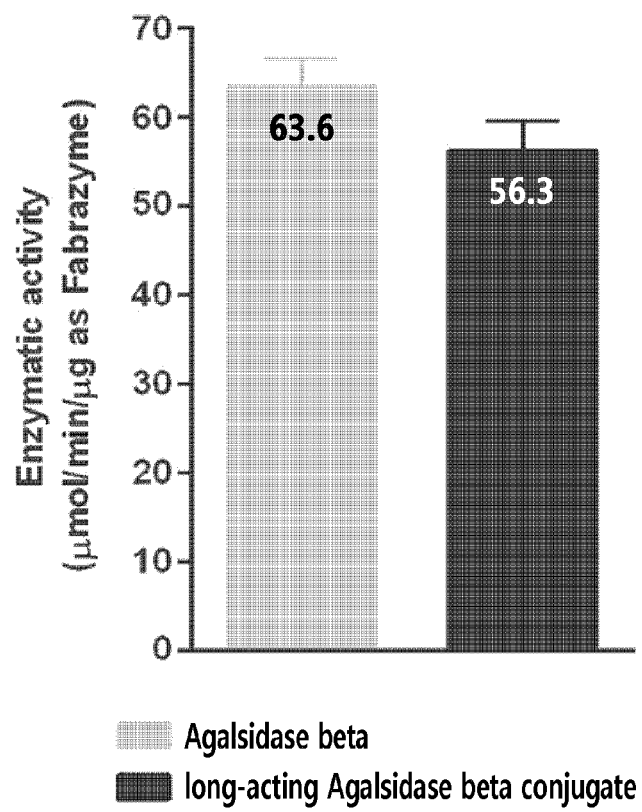

[FIG. 3]
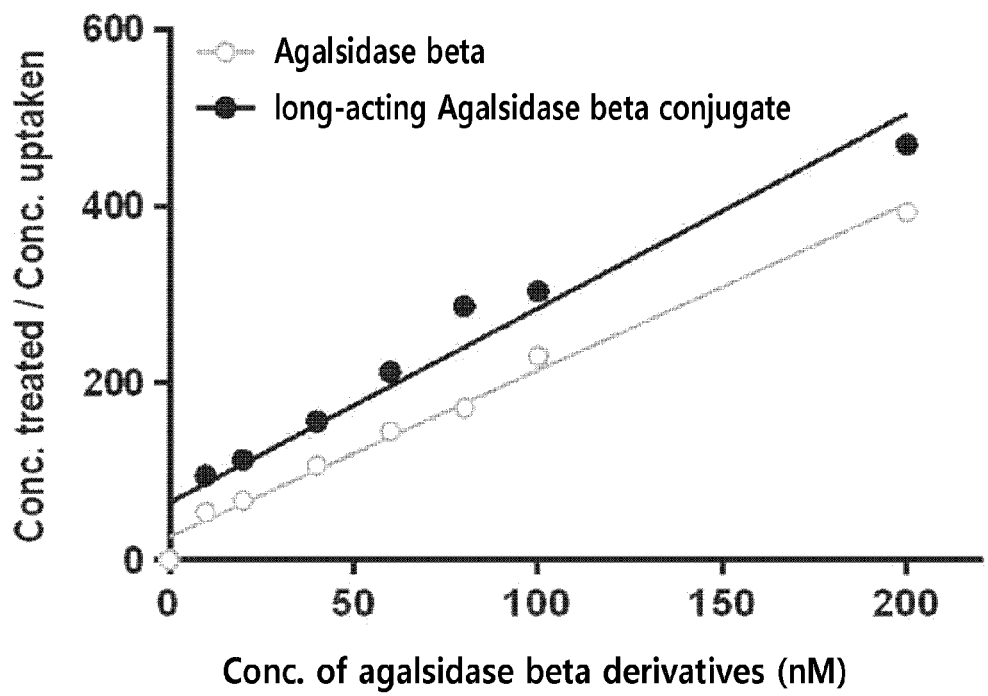

[FIG. 4]
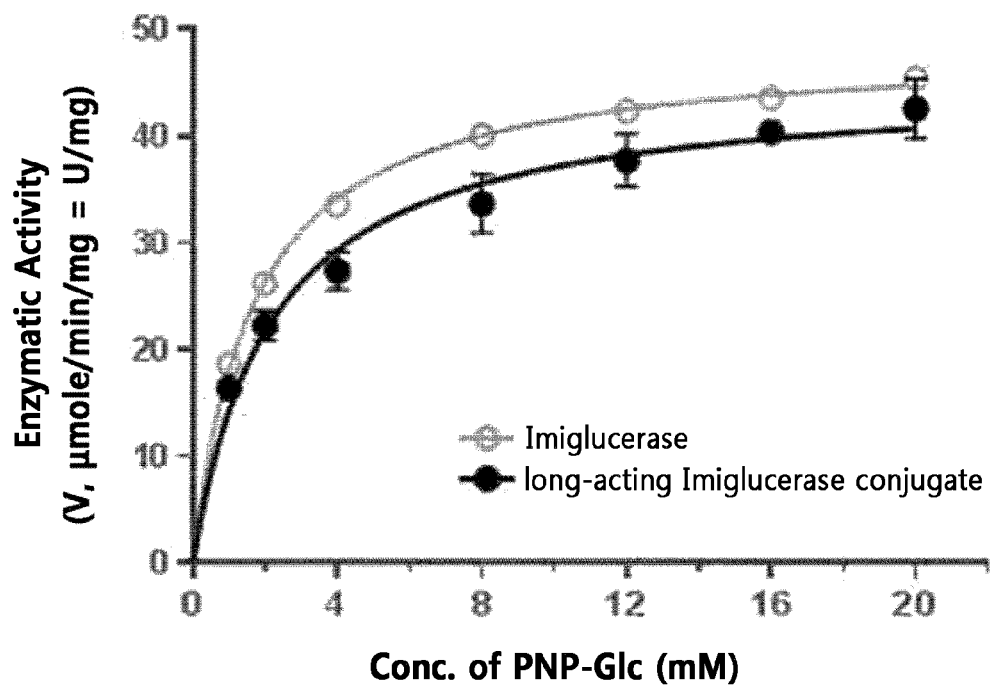

[FIG. 5]
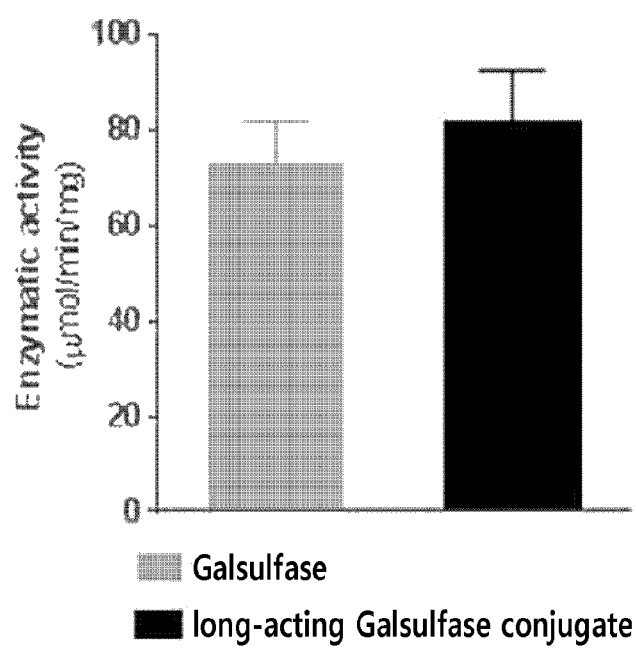

[FIG. 6]
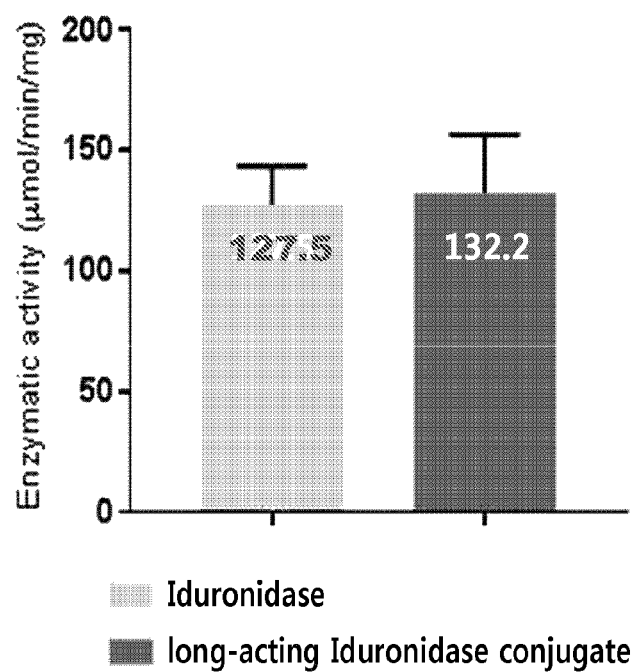

US 10,918,736 B2

CONJUGATE OF THERAPEUTIC ENZYMES

CROSS REFERENCE TO RELATED APPLICATIONS

This application is a National Stage of International Application No. PCT/KR2017/001016, filed on Jan. 31, 2017, which claims priority from Korean Patent Application No. 10-2016-0011886, filed on Jan. 29, 2016.

TECHNICAL FIELD

The present invention relates to a conjugate of therapeutic enzymes in which an immunoglobulin Fc region is linked to therapeutic enzymes through a non-peptide polymer linkage moiety, a method of preparing the conjugate, and a composition containing the conjugate.

BACKGROUND ART

Generally, proteins such as therapeutic enzymes have low stability and are thus easily modified and decomposed by protein hydrolases in the blood. Therefore, in order to maintain the blood concentration and potency of these proteins, it is necessary to frequently administer them to patients. However, in the case of protein drugs administered to patients mostly in the form of an injection, frequent injections to maintain the blood concentration of active polypeptides may cause excessive suffering in patients. To solve these problems, there has been a constant effort to maximize pharmacological efficacy by increasing the blood stability of the therapeutic enzymes and maintaining their blood concentration at a high level for a longer period of time. Such long-acting formulations of therapeutic enzymes are required to increase the stability of therapeutic enzymes and to simultaneously maintain the potency of the drugs themselves at a sufficiently high level, as well as to cause no immune reaction in patients.

In particular, lysosomal storage diseases (LSDs) are fatal disorders caused by genetic defects in particular enzymes that can lead to death, and replacement therapy is essential for the treatment of the defective enzymes (Frances M. Platt et al., J Cell Biol. 2012 Nov. 26; 199(5): 723-34). Enzyme replacement therapy is standard therapy in lysosomal storage diseases, and the therapy has an effect of alleviating the existing symptoms or delaying the progress of the disease by replacing the deficient enzyme. However, due to the requirement for continuous intravenous administration of a drug once every one or two weeks for 2 hours to 6 hours, the daily life of the patients and their family members may be restricted. Since the half-lives of the recombinant enzymes used for the treatment of lysosomal storage diseases in humans are very short to be in a range of 10 minutes to less than 3 hours, the recombinant enzymes are required to be administered life-time thus causing inconvenience to patients. Accordingly, it is of high necessity to extend the half-lives of the recombinant enzymes.

Additionally, there is an increasing need for the development of a therapeutic agent for lysosomal storage diseases due to the problems in that the in vivo storage locations of the enzymes used for the treatment of lysosomal storage diseases differ from each other, the therapeutic enzymes fail to arrive at the bone marrow, etc.

DISCLOSURE

Technical Problem

An object of the present invention is to provide an enzyme conjugate in which a therapeutic enzyme and an immunoglobulin Fc region are linked through a non-peptide polymer linkage moiety.

Another object of the present invention is to provide a pharmaceutical composition for preventing or treating lysosomal storage diseases containing the enzyme conjugate.

Still another object of the present invention is to provide a method for preparing the enzyme conjugate.

Technical Solution

An aspect of the present invention provides an enzyme conjugate, wherein a therapeutic enzyme for treating lysosomal storage disease (LSD) and an immunoglobulin Fc region are linked through a non-peptide polymer linkage moiety.

In a specific embodiment, the enzyme is selected from the group consisting of β-glucosidase, β-galactosidase, galactose-6-sulfatase, acid ceramidase, acid sphingomyelinase, galactocerebrosidase, arylsulfatase A, β-hexosaminidase A, β-hexosaminidase B, heparin N-sulfatase, α-D-mannosidase, β-glucuronidase, N-acetylgalactosamine-6 sulfatase, lysosomal acid lipase, α-N-acetyl-D-glucosaminidase (NAGLU), glucocerebrosidase, butyrylcholinesterase, chitinase, glutamate decarboxylase, lipase, uricase, platelet-activating factor acetylhydrolase, neutral endopeptidase, myeloperoxidase, acetyl-CoA-glucosaminide N-acetyltransferase, N-acetylglucosamine-6-sulfatase, galactosamine 6-sulfatase (GALN), hyaluronidase, α-fucosidase, β-mannosidase, α-neuraminidase (sialidase), N-acetyl-glucosamine-1-phosphotransferase, mucolipin-1, α-N-acetyl-galactosaminidase, N-aspartyl-β-glucosaminidase, LAMP-2, cystinosin, sialin, ceramidase, acid-β-glucosidase, galactosylceramidase, NPC1, cathepsin A, SUMF-1, lysosomal acid lipase (LIPA), and tripeptidyl peptidase 1.

Another aspect of the present invention provides an enzyme conjugate, wherein α-galactosidase A for treating lysosomal storage disease (LSD) and an immunoglobulin Fc region are linked through a non-peptide polymer linkage moiety.

Still another aspect of the present invention provides an enzyme conjugate, wherein arylsulfatase B (ARSB) for treating lysosomal storage disease (LSD) and an immunoglobulin Fc region are linked through a non-peptide polymer linkage moiety.

Still another aspect of the present invention provides an enzyme conjugate, wherein iduronidase for treating lysosomal storage disease (LSD) and an immunoglobulin Fc region are linked through a non-peptide polymer linkage moiety.

Still another aspect of the present invention provides an enzyme conjugate, wherein α-glucosidase for treating lysosomal storage disease (LSD) and an immunoglobulin Fc region are linked through a non-peptide polymer linkage moiety.

Still another aspect of the present invention provides an enzyme conjugate, wherein imiglucerase for treating lysosomal storage disease (LSD) and an immunoglobulin Fc region are linked through a non-peptide polymer linkage moiety.

In a specific embodiment, the present invention provides an enzyme conjugate wherein the lysosomal storage disease (LSD) is selected from the group consisting of mucopolysaccharidosis (MPS), glycogen storage disease, and sphingolipidosis.

In another specific embodiment, the present invention provides an enzyme conjugate wherein the mucopolysaccharidosis (MPS) is selected from the group consisting of mucopolysaccharidosis I (MPS I) and mucopolysaccharidosis VI (MPS VI).

In still another specific embodiment, the present invention provides an enzyme conjugate wherein the glycogen storage disease is Pompe disease.

In still another specific embodiment, the present invention provides an enzyme conjugate wherein the sphingolipidosis is selected from the group consisting of Fabry disease and Gaucher's disease.

In still another specific embodiment, the present invention provides an enzyme conjugate wherein the enzyme conjugate has increased transcytosis and bioavailability (BA) compared to the enzyme, to which an immunoglobulin Fc region is not linked.

In still another specific embodiment, the present invention provides an enzyme conjugate wherein the transcytosis is mediated by the binding between an immunoglobulin Fc region and a neonatal Fc receptor (FcRn).

In still another specific embodiment, the present invention provides an enzyme conjugate wherein the enzyme conjugate has an increased tissue distribution compared to the enzyme, to which an immunoglobulin Fc region is not linked.

In still another specific embodiment, the present invention provides an enzyme conjugate wherein the enzyme conjugate has an increased bone marrow targetability compared to the enzyme, to which an immunoglobulin Fc region is not linked.

In still another specific embodiment, the present invention provides an enzyme conjugate wherein the immunoglobulin Fc region is aglycosylated.

In still another specific embodiment, the present invention provides an enzyme conjugate wherein the immunoglobulin Fc region includes one to four domains selected from the group consisting of CH1, CH2, CH3, and CH4 domains.

In still another specific embodiment, the present invention provides an enzyme conjugate wherein the immunoglobulin Fc region includes a hinge region.

In still another specific embodiment, the present invention provides an enzyme conjugate wherein the immunoglobulin Fc region is an immunoglobulin Fc fragment derived from IgG, IgA, IgD, IgE, or IgM.

In still another specific embodiment, the present invention provides an enzyme conjugate wherein the immunoglobulin Fc region is a hybrid of domains having different origins derived from the immunoglobulins selected from the group consisting of IgG, IgA, IgD, IgE, and IgM.

In still another specific embodiment, the present invention provides an enzyme conjugate wherein the immunoglobulin Fc region is a dimer or multimer consisting of single-chain immunoglobulins composed of domains of the same origin.

In still another specific embodiment, the present invention provides an enzyme conjugate wherein the immunoglobulin Fc region is an IgG4 Fc fragment.

In still another specific embodiment, the present invention provides an enzyme conjugate wherein the immunoglobulin Fc region is a human aglycosylated IgG4 Fc fragment.

In still another specific embodiment, the present invention provides an enzyme conjugate wherein the enzyme conjugate is an enzyme conjugate where a non-peptide polymer linkage moiety is linked to the N-terminus of the enzyme.

Still another aspect of the present invention provides a pharmaceutical composition for preventing or treating lysosomal storage disease (LSD) containing the enzyme conjugate.

Still another aspect of the present invention provides a pharmaceutical composition for preventing or treating lysosomal storage disease (LSD) containing the α-galactosidase A conjugate.

Still another aspect of the present invention provides a pharmaceutical composition for preventing or treating lysosomal storage disease (LSD) containing the arylsulfatase B (ARSB) conjugate.

Still another aspect of the present invention provides a pharmaceutical composition for preventing or treating lysosomal storage disease (LSD) containing the iduronidase conjugate.

Still another aspect of the present invention provides a pharmaceutical composition for preventing or treating lysosomal storage disease (LSD) containing the α-glucosidase conjugate.

Still another aspect of the present invention provides a pharmaceutical composition for preventing or treating lysosomal storage disease (LSD) containing the imiglucerase conjugate.

In a specific embodiment, the present invention provides a pharmaceutical composition wherein the pharmaceutical composition increases transcytosis, bioavailability, tissue distribution, and bone marrow targetability.

Still another aspect of the present invention provides a method for preparing an enzyme conjugate, including:

(a) a step of linking a therapeutic enzyme for treating lysosomal storage disease (LSD) and a non-peptide polymer; and (b) a step of linking the linked material, where the enzyme and the non-peptide polymer are linked, and a biocompatible material capable of increasing the in vivo half-life of the enzyme.

In a specific embodiment, the present invention provides a method for preparing an enzyme conjugate, wherein the enzyme is selected from the group consisting of β-glucosidase, β-galactosidase, galactose-6-sulfatase, acid ceramidase, acid sphingomyelinase, galactocerebrosidase, arylsulfatase A, β-hexosaminidase A, β-hexosaminidase B, heparin N-sulfatase, α-D-mannosidase, β-glucuronidase, N-acetylgalactosamine-6 sulfatase, lysosomal acid lipase, α-N-acetyl-D-glucosaminidase (NAGLU), glucocerebrosidase, butyrylcholinesterase, chitinase, glutamate decarboxylase, lipase, uricase, platelet-activating factor acetylhydrolase, neutral endopeptidase, myeloperoxidase, acetyl-CoA-glucosaminide N-acetyltransferase, N-acetylglucosamine-6-sulfatase, galactosamine 6-sulfatase (GALN), hyaluronidase, α-fucosidase, β-mannosidase, α-neuraminidase (sialidase), N-acetyl-glucosamine-1-phosphotransferase, mucolipin-1, α-N-acetyl-galactosaminidase, N-aspartyl-β-glucosaminidase, LAMP-2, cystinosin, sialin, ceramidase, acid-β-glucosidase, galactosylceramidase, NPC1, cathepsin A, SUMF-1, lysosomal acid lipase (LIPA), and tripeptidyl peptidase 1.

Still another aspect of the present invention provides a method for preparing an enzyme conjugate, including:

(a) a step of linking α-galactosidase A for treating lysosomal storage disease (LSD) and a non-peptide polymer; and (b) a step of linking the linked material, where the α-galactosidase A and the non-peptide polymer are linked, and a biocompatible material capable of increasing the in vivo half-life of the enzyme.

Still another aspect of the present invention provides a method for preparing an enzyme conjugate, including:

(a) a step of linking arylsulfatase B (ARSB) for treating lysosomal storage disease (LSD) and a non-peptide polymer; and (b) a step of linking the linked material, where the arylsulfatase B (ARSB) and the non-peptide polymer are linked, and a biocompatible material capable of increasing the in vivo half-life of the enzyme.

Still another aspect of the present invention provides a method for preparing an enzyme conjugate, including:

(a) a step of linking iduronidase for treating lysosomal storage disease (LSD) and a non-peptide polymer; and (b) a step of linking the linked material, where the iduronidase and the non-peptide polymer are linked, and a biocompatible material capable of increasing the in vivo half-life of the enzyme.

Still another aspect of the present invention provides a method for preparing an enzyme conjugate, including:

(a) a step of linking α-glucosidase for treating lysosomal storage disease (LSD) and a non-peptide polymer; and (b) a step of linking the linked material, where the α-glucosidase and the non-peptide polymer are linked, and a biocompatible material capable of increasing the in vivo half-life of the enzyme.

Still another aspect of the present invention provides a method for preparing an enzyme conjugate, including:

(a) a step of linking imiglucerase for treating lysosomal storage disease (LSD) and a non-peptide polymer; and (b) a step of linking the linked material, where the imiglucerase and the non-peptide polymer are linked, and a biocompatible material capable of increasing the in vivo half-life of the enzyme.

In a specific embodiment, the present invention provides a method for preparing an enzyme conjugate, wherein the non-peptide polymer is selected from the group consisting of polyethylene glycol, polypropylene glycol, an ethylene glycol/propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, and a combination thereof.

In another specific embodiment, the present invention provides a method for preparing an enzyme conjugate, wherein the non-peptide polymer is polyethylene glycol.

In still another specific embodiment, the present invention provides a method for preparing an enzyme conjugate, wherein the reactive group of the non-peptide polymer of step (a) is selected from the group consisting of an aldehyde group, a maleimide group, and a succinimide derivative.

In still another specific embodiment, the present invention provides a method for preparing an enzyme conjugate, wherein the aldehyde group is a propionaldehyde group or butyraldehyde group.

In still another specific embodiment, the present invention provides a method for preparing an enzyme conjugate, wherein the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In still another specific embodiment, the present invention provides an enzyme conjugate, wherein the non-peptide polymer has an aldehyde group as a reactive group at both ends.

In still another specific embodiment, the present invention provides an enzyme conjugate, wherein the non-peptide polymer has an aldehyde group and a maleimide group as a reactive group at both ends, respectively.

In still another specific embodiment, the present invention provides an enzyme conjugate, wherein the non-peptide polymer has an aldehyde group and a succinimide group as a reactive group at both ends, respectively.

In still another specific embodiment, the present invention provides a method for preparing an enzyme conjugate, wherein the method further includes a step of isolating a linked material, to which a non-peptide polymer linkage moiety is linked to the N-terminus of the enzyme.

Advantageous Effects of the Invention

The present invention relates to a therapeutic enzyme conjugate, and specifically to an enzyme conjugate, in which a therapeutic enzyme, a non-peptide polymer linkage moiety, and an immunoglobulin Fc are linked together by covalent bonds, thereby having enhanced transcytosis, in vivo bioavailability, tissue distribution, and bone marrow targetability as well as in vivo duration of the enzyme. The enzyme conjugate prepared by the present invention can be effectively used for the treatment of lysosomal storage disease (LSD).

BRIEF DESCRIPTION OF DRAWINGS

FIG. 1 shows the results of PK experiments for a agalsidase beta conjugate.

FIG. 2 shows the results of in vitro enzyme activity for a agalsidase beta conjugate.

FIG. 3 shows the results of in vitro intracellular uptake activity for a long-acting agalsidase beta conjugate.

FIG. 4 shows the results of in vitro enzyme activity for a imiglucerase conjugate.

FIG. 5 shows the results of in vitro enzyme activity for a galsulfase conjugate.

FIG. 6 shows the results of in vitro enzyme activity for a iduronidase conjugate.

DETAILED DESCRIPTION OF THE INVENTION

Hereinbelow, exemplary embodiments of the present invention will be described in detail. Meanwhile, each of the explanations and exemplary embodiments disclosed herein can be applied to other explanations and exemplary embodiments. That is, all the combinations of various factors disclosed herein belong to the scope of the present invention. Furthermore, the scope of the present invention should not be limited by the specific disclosure provided hereinbelow.

In order to achieve the above objects, an aspect of the present invention provides an enzyme conjugate, wherein a therapeutic enzyme for treating lysosomal storage disease (LSD) and an immunoglobulin Fc region are linked through a non-peptide polymer linkage moiety.

Specifically, the enzyme conjugate may be an enzyme conjugate in which the non-peptide polymer linkage moiety is linked to an immunoglobulin Fc region and the enzyme.

In a specific embodiment of the present invention, the enzyme conjugate is one which is obtained by reacting a non-peptide polymer with a free Fc region and a free enzyme, in which the non-peptide polymer is the same material as the non-peptide polymer linkage moiety in terms of the kinds, numbers, and locations of the repeating units. The non-peptide polymer used in the reaction of the free Fc region and free enzyme may be a material which has reactive end groups at both ends of the repeating units having a chemical structure different from those of the repeating units. In such a process for preparing an enzyme conjugate, enzyme conjugates where the repeating units of a non-peptide polymer are linked to an enzyme and an Fc region through a covalent bond generated while the reactive end groups are converted by chemical reactions, where each of the chemical reactions within a free enzyme and a free immunoglobulin Fc region is caused through reactive end groups of the non-peptide polymer, are obtained. That is, in a specific embodiment of the present invention, the non-peptide polymer is converted into a non-peptide polymer linkage moiety within the enzyme conjugates through the preparation process.

The enzyme that can be included in the enzyme conjugate of the present invention is not particularly limited, but any enzyme which can obtain an advantage by extending its in vivo duration by preparing it into the enzyme conjugate of the present invention, rather than an enzyme in an unconjugated form, can be included. In an exemplary embodiment of the present invention, the enzyme conjugate is a conjugate of a therapeutic enzyme.

Specifically, the enzyme conjugate may be one in which the enzyme is selected from the group consisting of β-glucosidase, β-galactosidase, galactose-6-sulfatase, acid ceramidase, acid sphingomyelinase, galactocerebrosidase, arylsulfatase A, β-hexosaminidase A, β-hexosaminidase B, heparin N-sulfatase, α-D-mannosidase, β-glucuronidase, N-acetylgalactosamine-6 sulfatase, lysosomal acid lipase, α-N-acetyl-D-glucosaminidase (NAGLU), glucocerebrosidase, butyrylcholinesterase, chitinase, glutamate decarboxylase, lipase, uricase, platelet-activating factor acetylhydrolase, neutral endopeptidase, myeloperoxidase, acetyl-CoA-glucosaminide N-acetyltransferase, N-acetylglucosamine-6-sulfatase, galactosamine 6-sulfatase (GALN), hyaluronidase, α-fucosidase, β-mannosidase, α-neuraminidase (sialidase), N-acetyl-glucosamine-1-phosphotransferase, mucolipin-1, α-N-acetyl-galactosaminidase, N-aspartyl-β-glucosaminidase, LAMP-2, cystinosin, sialin, ceramidase, acid-β-glucosidase, galactosylceramidase, NPC1, cathepsin A, SUMF-1, lysosomal acid lipase (LIPA), and tripeptidyl peptidase 1, but any enzyme which can treat lysosomal storage disease (LSD) can be included in the present invention without limitation, regardless of the kind or origin of the enzyme.

Another aspect of the present invention provides an enzyme conjugate, wherein α-galactosidase A for treating lysosomal storage disease (LSD) and an immunoglobulin Fc region are linked through a non-peptide polymer linkage moiety.

Still another aspect of the present invention provides an enzyme conjugate, wherein arylsulfatase B (ARSB) for treating lysosomal storage disease (LSD) and an immunoglobulin Fc region are linked through a non-peptide polymer linkage moiety.

Still another aspect of the present invention provides an enzyme conjugate, wherein iduronidase for treating lysosomal storage disease (LSD) and an immunoglobulin Fc region are linked through a non-peptide polymer linkage moiety.

Still another aspect of the present invention provides an enzyme conjugate, wherein α-glucosidase for treating lysosomal storage disease (LSD) and an immunoglobulin Fc region are linked through a non-peptide polymer linkage moiety.

Still another aspect of the present invention provides an enzyme conjugate, wherein imiglucerase for treating lysosomal storage disease (LSD) and an immunoglobulin Fc region are linked through a non-peptide polymer linkage moiety.

As used herein, the term "therapeutic enzyme" or "enzyme" refers to an enzyme for treating diseases that occur due to lack of the enzyme, deficiency, functional disorders, etc., and the enzyme can treat a subject with the diseases by enzyme replacement therapy, administration, etc. Specifically, the enzyme may be an enzyme for treating diseases that may occur due to the lack, deficiency, etc., of lysosomal enzyme, but is not limited thereto.

As used herein, the term "lysosome", being one of the organelles present in the cytoplasm, contains many hydrolases and decomposes unwanted materials in the body such as macromolecules, bacteria, etc., and helps the decomposed products to be utilized in other parts of cells. The functions of a lysosome can be performed by many enzymes. When a particular enzyme loses its function due to a mutation, deficiency, etc., it causes the loss of the decomposing function of the lysosome and results in the accumulation of macromolecules, etc., which must be decomposed, in the cell and induce cell damage or the like thereby causing a disease.

As used herein, the term "lysosomal storage disease (LSD)" refers to a rare genetic disease due to the loss of lysosomal functions described above, and enzymatic replacement therapy is essential for a supplement for the defective or deficient enzyme. In the present invention, the term "lysosomal storage disease" can be used interchangeably with "lysosomal storage disorder". The lysosomal storage disease can be classified based on the defective or deficient enzyme into: (i) sphingolipidosis, (ii) mucopolysaccharidosis, (iii) glycogen storage disease, (iv) mucolipidosis, (v) oligosaccharidosis, (vi) lipidosis, (vii) lysosomal transport disease, etc.

Hereinafter, the lysosomal storage disease will be described in detail according to its classification.

As used herein, the term "sphingolipidosis" refers to a genetic deficiency syndrome of lysosomal enzyme which hydrolyzes the sugar side chains or choline side chains of sphingolipids. Diseases classified according to the distribution of each storage lipid, such as Krabbe disease caused by the deficiency of galactocerebrosidase, Fabry disease caused by the deficiency of α-galactosidase A, Niemann-Pick disease caused by the deficiency of sphingomyelinase, Gaucher's disease caused by the deficiency of glucocerebrosidase, Tay-Sachs disease caused by the deficiency of hexosaminidase A, etc., are included therein, and they correspond to autosomal reccessive inheritance disease, except Fabry disease which is an X-linked genetic disease.

As used herein, the term "Fabry disease (also known as Fabry's disease)" refers to a disease of an inborn error of glycolipid metabolism caused by lack of activity of α-galactosidase A, which is a hydrolase present in lysosomes, and it is a genetic disease of X-linked recessive inheritance. Fabry's disease shows no distinct symptoms during the early childhood but pains at four limbs and eczema, etc. appear from childhood, and cardiovascular manifestations and renal disorders appear after the adolescence. Its treatment may include enzymatic replacement therapy, gene therapy, etc.

As used herein, the term "Gaucher's disease" refers to a disease of an inborn error of lipid metabolism caused by lack of glucocerebrosidase due to genetic disorder, and specifically, it is an autosomal (chromosome No. 1) recessive genetic disorder. The disease is caused by the accumulation of old cells in the liver, spleen, and bone marrow. In a severe case, it is known that the disease may be metastasized into the eyes, kidneys, heart, and nervous systems and thereby cause complications. Its treatment may include enzymatic replacement therapy, gene therapy, etc.

As used herein, the term "mucopolysaccharidosis (MPS)" refers to a syndrome of genetic hydrolase deficiency of mucous polysaccharides, and it is known to be caused by the deficiency of a sugar chain-decomposing enzyme, sulfatase, acetyltransferase, etc., and is also called gargoylis. The major symptom of mucopolysaccharidosis (MPS) is an excessive excretion of mucopolysaccharides in the urine. At present, MPS can be classified into 6 disease types, in which type I includes Hurler syndrome and Scheie syndrome; type II includes Hunter syndrome; type III includes Sanfilippo syndrome types A, B, C, and D; type IV includes Morquio syndrome A and B; and type VI includes Maroteaux-Lamy syndrome; and type VII includes Sly syndrome.

As used herein, the term "Hurler syndrome" is a disease that belongs to type I mucopolysaccharidosis (MPS) caused by the deficiency of α-L-iduronidase, which is a hydrolase of mucopolysaccharides, and it is a rare autosomal recessive genetic disease. Hurler syndrome shows symptoms similar to those of Hunter syndrome but more severely, and most of the patients with Hurler syndrome die before age 10. Hurler syndrome accompanies corneal opacity, in addition to the symptoms of Hunter syndrome, such as intellectual disability, deafness, enlargement of the liver and spleen, physical characteristics such as a low nose bridge, thick lips, a large tongue, etc., and severe skeletal malformation, etc.

As used herein, the term "Maroteaux-Lamy syndrome", which belongs to type VI mucopolysaccharidosis (MPS) diseases, is an autosomal recessive genetic disease that occurs due to the deficiency of arylsulfatase B (N-acetylgalactosamine-4-sulfatase) necessary for the breakdown of glycosaminoglycan. Maroteaux-Lamy syndrome is a disease that occurs by the deposition of dermatan sulfate which was not decomposed due to the deficiency of the enzyme in the bones, cardiac valves, spleen, liver, cornea, etc.

As used herein, the term "glycogen storage disease (also known as glycogenosis)" refers to a disease of an inborn error of carbohydrate metabolism caused by the accumulation of glycogen and is known to be classified into I to VII subtypes. The subtypes of glycogen storage disease associated with lysosomal storage disease (LSD) are types II (Pompe disease) and III b (Danon disease).

The type II glycogen storage disease is called acid maltase deficiency or Pompe disease, and it is a disease caused by the deficiency of α-glucosidase (α-1,4-glucosidase, or acid α-glucosidase), and the patients are known to experience enlargement of the liver and kidney, muscle weakness, enlargement of tongue, enlargement of heart, dyspnea, etc., and die within several months.

As used herein, the term "therapeutic enzyme conjugate for the treatment of lysosomal storage disease (LSD)" or "enzyme conjugate" refers to one where an enzyme having the effect of treating the lysosomal storage disease is linked to an immunoglobulin Fc region through a non-peptide polymer linkage moiety, and the conjugate can provide the effect of preventing or treating the lysosomal storage disease by the enzyme.

The enzyme conjugates of the present invention can provide an enhanced duration by linking a material capable of increasing the half-life of the therapeutic enzyme to the enzyme. As such, the term "enzyme conjugate" of the present invention can be used interchangeably with "long-acting conjugate".

Additionally, the enzyme conjugates of the present invention can be used as a medicament for enzymatic replacement therapy (ERT). The enzymatic replacement therapy can be used for preventing or treating diseases via restoration of the deteriorated enzyme function by replenishing the depleted or deficient enzyme that becomes the cause of the subject disease.

Specifically, the enzyme conjugate of the present invention, where the Fc region is linked to an FcRn, has the effect of an enhanced transcytosis activity compared to the enzyme which is not linked to the Fc region.

The enhanced transcytosis mediated by FcRn, although the enzyme is linked to an Fc region and forms a large molecule, can not only help to maintain intracellular uptake rate but also help the therapeutic enzyme to treat lysosomal storage disease by performing the function of the enzyme itself by being absorbed into the body while maintaining the enzyme activity for a long period of time.

Meanwhile, therapeutic enzymes, especially the ERT enzymes used for the lysosomal storage disease (LSD) have a low in vivo bioavailability (BA) and thus they have a problem in that they must be administered via intravenous injection. The intravenous injection causes inconveniences that require patients to visit a hospital for each intravenous injection. Additionally, the intravenous injection can induce an allergic-type hypersensitive reaction thereby causing side-effects (infusion reaction) associated with frequent injection of medicaments.

Due to the increased bioavailability caused by the transcytosis by the FcRn-binding region, the enzyme conjugate of the present invention enables subcutaneous injection instead of intravenous injection, and such change in administration enables self-injection and thus increase patient convenience and lowers the infusion reaction thereby minimizing side-effects.

Additionally, for the therapeutic enzymes, especially the ERT enzymes used for the lysosomal storage disease (LSD), it is necessary to remove wastes built-up in particular tissue and thus the uniform distribution into each tissue is very important. However, the ERT enzymes currently in use mostly show a higher degree of distribution in the liver, and thus it is essential to develop a medicament that can provide a relatively uniform distribution into various organs in the body.

The enzyme conjugates of the present invention have excellent distribution by having high in vivo concentration in various tissues other than the liver, in particular, in the bone marrow, spleen, kidney, etc., due to the increased half-life in the blood and transcytosis by the FcRn-binding region, thus being capable of maximizing therapeutic efficiency. In particular, the enzyme conjugates of the present invention have high bone marrow targetability. The bone marrow is a tissue with a soft structure present inside of a bone, and an additional effect can be expected through a pharmacological action in the bone marrow by the enzymatic replacement therapy by increasing the targetability to the bone marrow tissue, and thus the lysosomal storage disease can be effectively treated.

In particular, the lysosomal storage disease occurs in various organs in the body, and especially, the lysosomal storage disease in bone marrow causes various side effects including abnormal symptoms of bones, inhibition of ossifications, or anemia through the inhibition of the erythropoietic hormone and thrombopoietic hormone, which must be essentially produced in the bone marrow. However, the commercial therapeutic enzyme treatments currently available have a very low level of distribution in the bone marrow thus frequently causing the side effects described above. In this regard, the enzyme conjugates of the present invention, due to the high bone marrow targetability, can be used as an excellent therapeutic agent for enzymatic replacement therapy.

Accordingly, the enzyme conjugates of the present invention, by binding between immunoglobulin Fc region and an FcRn, may have an enhanced transcytosis, bioavailability, tissue distribution, and bone marrow targetability, compared to the enzyme which is not linked to an immunoglobulin Fc region.

The therapeutic enzymes to be included in the enzyme conjugates of the present invention may include without limitation any enzyme that has the effect of treating the lysosomal storage disease, and specifically include the enzymes described below.

As used herein, the term "α-galactosidase A", also called aglasidase, refers to an enzyme which is associated with Fabry disease, and it is an enzyme hydrolyzing the terminal α-galactosyl moieties of glycolipids or glycoproteins into galactose and glucose. In the present invention, the term α-galactosidase A may be used interchangeably with α-galactosidase or agalsidase. The α-galactosidase or agalsidase may be agalsidase α or agalsidase β.

As used herein, the term "imiglucerase" refers to an enzyme having the activity of a glycosylceramide-hydrolyzing enzyme and an enzyme hydrolyzing the β-glucosidic linkage of glucocerebroside, which is an intermediate of glycolipid metabolism, and is in a recombinant form of human β-glucocerebrosidase. Imiglucerase is known to be associated with Gaucher's disease.

As used herein, "iduronidase", also called L-iduronidase, α-L-iduronidase (IDUA), or laronidase, is involved in the hydrolysis of glycosaminoglycans such as dermatan sulfate and heparan sulfate. In the present invention, the term iduronidase may be used interchangeably with laronidase.

As used herein, the term "arylsulfatase B (ARSB)" refers to an arylsulfatase which is present in the lysosomes of the liver, pancreas, and kidneys, and the enzyme has the role of hydrolyzing sulfates by decomposing glycosaminoglycan. The arylsulfatase B is known to be associated with mucopolysaccharidosis VI (Maroteaux-Lamy syndrome). In the present invention, the term arylsulfatase B may be used interchangeably with galsulfase.

As used herein, the term "α-glucosidase" refers to a kind of glucosidases that are involved in the breakdown of starch or disaccharides into glucose, and the deficiency of α-glucosidase causes the occurrence of Pompe disease. In the present invention, the term α-glucosidase may be used interchangeably with alglucosidase or acid α-glucosidase (GAA).

In an exemplary embodiment of the present invention, conjugates where enzymes for the treatment of lysosomal storage disease, such as agalsidase, imiglucerase, galsulfase, and laronidase, were linked to an immunoglobulin Fc region and a non-peptide polymer, respectively, were prepared (Example 3), and the in vitro and in vivo activities of each of the enzyme conjugates were confirmed (Examples 4 to 8).

As a result, it was confirmed that the enzymes for each of enzyme conjugates were shown to have an increase in all of half-life, transcytosis, bioavailability, tissue distribution, and bone marrow targetability while maintaining their enzyme activities, although the enzymes were linked to an Fc region.

The therapeutic enzymes that can be included in the enzyme conjugates of the present invention may be in their native form, and additionally, fragments composed of part of the enzymes, or enzyme analogs thereof, in which a variant selected from the group consisting of substitution, addition, deletion, modification of some amino acids, and a combination thereof occurred, may be included without limitation, as long as they have the same enzyme activity as those in their native forms.

The enzyme analogs may include the biosimilars and biobetters of the corresponding enzymes. For example, with respect to biosimilars, in consideration of the difference between a known enzyme and a host for its expression, the difference in glycosylation feature and the degree thereof, and the difference in the degree of substitution in a particular amino acid residue of the corresponding enzyme in light of the standard sequence where the degree of substitution is not 100% substitution, they belong to the biosimilar enzymes. The enzymes may be produced by genetic recombination in animal cells, E. coli, yeast, insect cells, plant cells, and in live animals, etc., and the preparation method is not limited thereto, and the enzymes may be commercially available enzymes.

Additionally, the enzymes may include an amino acid sequence which have a homology of at least 80%, more specifically 90%, and even more specifically 91%, 92%, 93%, 94%, 95%, 96%, 97%, 98%, or 99% or higher to that of the above enzymes or analogs thereof, and the enzymes may be obtained from microorganisms by recombinant technology or those which are commercially available, but are not limited thereto.

As used herein, the term "homology" represents the degree of similarity to the amino acid sequence of a wild-type protein or a nucleotide sequence encoding the amino acids, and it includes those sequences which have the same sequence at a percentage level described above to the amino acid sequences or nucleotide sequences of the present invention. The homology may be determined by comparing the two given sequences by the naked eye or may be determined using a bioinformatic algorithm, which enables the analysis of a homology by arranging the subject sequences for comparison. The homology between the two given amino acid sequences may be indicated as a percentage. The useful automated algorithm is available for use in GAP, BESTFIT, FASTA, and TFASTA computer software modules of Wisconsin Genetics Software Package (Genetics Computer Group, Madison, Wis., USA). The arrangement algorithm automated in the above modules includes sequence arrangement algorithms by Needleman & Wunsch, Pearson & Lipman, and Smith & Waterman. Other useful algorithms on sequence arrangement and homology determination are automated in software including FASTP, BLAST, BLAST2, PSIBLAST, and CLUSTAL W.

The amino acid sequences and nucleotide sequences encoding the same of the enzymes and analogs thereof may be obtained from a known database such as the GenBank of NCBI, but are not limited thereto.

As used herein, the term "immunoglobulin Fc region" refers to a region of an immunoglobulin molecule, except for the variable regions of the heavy and light chains, the heavy-chain constant region 1 ($C_H1$) and the light-chain constant region 1 ($C_L1$) of an immunoglobulin. The immunoglobulin Fc region may further include a hinge region at the heavy-chain constant region. In particular, the immunoglobulin Fc region of the present invention may be a fragment including a part or entirety of the Fc region, and in the present invention, the immunoglobulin Fc region may be used interchangeably with an immunoglobulin fragment.

A native Fc has a sugar chain at position Asn297 of heavy-chain constant region 1, but E. coli-derived recombinant Fc is expressed as an aglycosylated form. The removal of sugar chains from Fc results in a decrease in binding affinity of Fc gamma receptors 1, 2, and 3 and complement (c1q) to heavy-chain constant region 1, leading to a decrease or loss in antibody-dependent cell-mediated cytotoxicity or complement-dependent cytotoxicity.

As used herein, the term "immunoglobulin constant region" may refer to an Fc fragment including heavy-chain constant region 2 (CH2) and heavy-chain constant region 3 (CH3) (or containing heavy-chain constant region 4 (CH4)), except for the variable regions of the heavy and light chains, the heavy-chain constant region 1 (CH1) and the light-chain constant region (CL) of an immunoglobulin, and may further include a hinge region at the heavy chain constant region. Further, the immunoglobulin constant region of the present invention may be an extended immunoglobulin constant region including a part or entirety of the Fc region including the heavy-chain constant region 1 (CH1) and/or the light-chain constant region (CL), except for the variable regions of the heavy and light chains of an immunoglobulin, as long as it has a physiological function substantially similar to or better than the native protein. Also, it may be a region having deletion in a relatively long portion of the amino acid sequence of CH2 and/or CH3. That is, the immunoglobulin constant region of the present invention may include (1) a CH1 domain, a CH2 domain, a CH3 domain, and a CH4 domain, (2) a CH1 domain and a CH2 domain, (3) a CH1 domain and a CH3 domain, (4) a CH2 domain and a CH3 domain, (5) a combination of one or more domains of the constant region and an immunoglobulin hinge region (or a portion of the hinge region), and (6) a dimer of each domain of the heavy-chain constant regions and the light-chain constant region. An immunoglobulin constant region including the immunoglobulin Fc fragment is a biodegradable polypeptide which can be metabolized in vivo and thus it can safely be used as a drug carrier. In addition, an immunoglobulin Fc fragment is more advantageous in terms of production, purification, and yield of a complex than an entire immunoglobulin molecule, owing to its relatively low molecular weight. Further, since it is devoid of Fab, which exhibits high non-homogeneity due to the difference in amino acid sequence from one antibody to another, it is expected to significantly enhance homogeneity and to reduce the possibility of inducing blood antigenicity.

Meanwhile, the immunoglobulin constant region may originate from humans or animals, such as cows, goats, pigs, mice, rabbits, hamsters, rats, guinea pigs, etc., and may preferably be of human origin. In addition, the immunoglobulin constant region may be selected from the group consisting of constant regions derived from IgG, IgA, IgD, IgE, IgM, or combinations or hybrids thereof, specifically, derived from IgG or IgM, which are the most abundant thereof in human blood, and most specifically, derived from IgG, which is known to improve the half-life of ligand-binding proteins. In the present invention, the immunoglobulin Fc region may be a dimer or multimer consisting of single-chain immunoglobulins composed of domains of the same origin.

As used herein, the term "combination" means that polypeptides encoding single chain immunoglobulin constant regions (specifically Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single-chain of an immunoglobulin constant region (preferably, an Fc region). In the present invention, various hybrid forms are possible. That is, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof, specifically, the IgG2 and IgG4 subclasses, and more specifically, the Fc region of IgG4 which rarely has effector functions such as complement dependent cytotoxicity (CDC).

The immunoglobulin constant region may have the glycosylated form to the same extent as, or to a greater or lesser extent than the native form or may be the deglycosylated form. Increased or decreased glycosylation or deglycosylation of the immunoglobulin constant region may be achieved by conventional methods, e.g., a chemical method, an enzymatic method, or a genetic engineering method using microorganisms. Herein, when deglycosylated, the complement (C1q) binding to an immunoglobulin constant region becomes significantly decreased and antibody-dependent cytotoxicity or complement-dependent cytotoxicity is reduced or removed, thereby not inducing unnecessary immune responses in vivo. In this regard, deglycosylated or aglycosylated immunoglobulin constant regions are more consistent with the purpose of drug carriers. Accordingly, the immunoglobulin Fc region may be even more specifically an aglycosylated Fc region derived from human IgG4, i.e., a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For example, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., C1q fixation sites or ADCC sites may be eliminated to remove the effector function. The techniques of preparing the sequence derivatives of the immunoglobulin constant region are disclosed in International Patent Publication Nos. WO 97/34631 and WO 96/32478, etc.

Amino acid substitutions in a protein or peptide molecule that do not alter the activity of a molecule are well known in the art (H. Neurath, R. L. Hill, The Proteins, Academic Press, New York, 1979). The most common substitutions occur between amino acid residues Ala/Ser, Val/Ile, Asp/

Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly, in both directions. Optionally, amino acids may be modified by phosphorylation, sulfation, acrylation, glycosylation, methylation, farnesylation, acetylation, amidation, etc.

The above-described immunoglobulin constant region derivative may be a derivative which has the same biological activity as that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a protease. Papain digests the native immunoglobulin into Fab and Fc regions, and pepsin treatment results in the production of pF'c and F(ab)2 fragments. These fragments may be subjected to size exclusion chromatography to isolate Fc or pF'c.

Preferably, a human-derived immunoglobulin constant region may be a recombinant immunoglobulin constant region that is obtained from a microorganism.

As used herein, the term "non-peptide polymer" includes a biocompatible polymer to which at least two repeating units are linked, and may be used interchangeably with "non-peptide linker". The repeating units are linked together through a random covalent bond instead of a peptide bond. In the present invention, the non-peptide polymer may form a conjugate through a reaction with other element(s) which constitute(s) the conjugate, by including a reactive group(s) at an end thereof.

As used herein, the term "non-peptide polymer linkage moiety" refers to a constituting element in a conjugate, which was formed by linking a non-peptide polymer having reactive groups at both ends to an immunoglobulin Fc region and a therapeutic enzyme through each reactive group of the non-peptide polymer.

In a specific embodiment of the present invention, the enzyme conjugate may be one in which an immunoglobulin Fc region and a therapeutic enzyme are linked together through a non-peptide polymer, which includes at both ends reactive groups that can be linked to the immunoglobulin Fc region and therapeutic enzyme.

Specifically, although not particularly limited thereto, the non-peptide polymer may be one selected from the group consisting of polyethylene glycol, polypropylene glycol, an ethylene glycol-propylene glycol copolymer, polyoxyethylated polyol, polyvinyl alcohol, a dextran, polyvinyl ethyl ether, a biodegradable polymer such as polylactic acid (PLA) and polylactic-glycolic acid (PLGA), a lipid polymer, chitins, hyaluronic acid, an oligonucleotide, and a combination thereof. In a more specific embodiment, the non-peptide polymer may be polyethylene glycol, but is not limited thereto. Additionally, the derivatives of the above materials already known in the art and the derivatives that can be easily produced at the technology level in the art also belong to the scope of the present invention.

The molecular weight of the non-peptide polymer may be in the range of exceeding 0 kDa to 200 kDa, and specifically, 1 kDa to 100 kDa, more specifically, 1 kDa to 50 kDa, even more specifically, 1 kDa to 20 kDa, even more specifically, 3.4 kDa to 10 kDa, even yet more specifically, about 3.4 kDa, but is not limited thereto.

In a specific embodiment of the present invention, both ends of the non-peptide polymer may be linked to an amine or thiol group of an immunoglobulin Fc region; or to an amine or thiol group of a therapeutic enzyme, respectively.

Specifically, the non-peptide polymer may include at both ends reactive groups that can be linked to an immunoglobulin Fc and a therapeutic enzyme, respectively, and specifically, the reactive groups that can be linked to an amine group of lysine, a thiol group of cysteine, or the N-terminus of the immunoglobulin Fc or therapeutic enzyme, but is not limited thereto.

More specifically, the reactive groups of the non-peptide polymer may be selected from the group consisting of an aldehyde group, a maleimide group, and a succinimide derivative, but is not limited thereto.

In the above, examples of the aldehyde group may include a propionaldehyde group or butyraldehyde group, but are not limited thereto.

In the above, as a succinimide derivative, succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate may be used, but the succinimide derivative is not limited thereto.

The non-peptide linker may be linked to an immunoglobulin Fc and a therapeutic enzyme through the reactive groups and converted into a non-peptide polymer linkage moiety.

Additionally, the final product produced through reductive alkylation by an aldehyde bond is more stable than that linked by an amide bond. The aldehyde reactive group selectively reacts with a N-terminus at a low pH condition while it can form a covalent bond with a lysine residue at high pH (e.g., pH 9.0).

The reactive groups at both ends of the non-peptide polymer may be the same or different from each other, and in addition, the non-peptide polymer may have aldehyde groups at both ends; an aldehyde group and a maleimide group as a reactive group at both ends, respectively; or an aldehyde group and a succinimide group as a reactive group at both ends, respectively, but the reactive groups are not limited thereto.

For example, the non-peptide polymer may have a maleimide group at one end and an aldehyde group, propionaldehyde group, or butyraldehyde group at the other end. For another example, the non-peptide polymer may have a succinimidyl group at one end and a propionaldehyde group or butyraldehyde group at the other end.

When poly(ethylene glycol) having a hydroxy reactive group at the propion-side end is used as a non-peptide polymer, the enzyme conjugates of the present invention may be prepared by activating the hydroxy group into various reactive groups by a known chemical reaction or using the poly(ethylene glycol) having a commercially-obtainable modified reactive group.

In a specific embodiment, the non-peptide polymer may be one in which a reactive group of the non-peptide polymer can be linked to a cysteine residue of a therapeutic enzyme, and more specifically, to the —SH group of cysteine, but is not limited thereto.

When maleimide-PEG-aldehyde is used, the maleimide group may be linked to the —SH group of a therapeutic enzyme by a thioether bond, and the aldehyde group may be linked to the —NH$_2$ group of the immunoglobulin Fc through reductive alkylation, but is not limited thereto, and this is merely an embodiment.

Through the reductive alkylation, a structure like -PEG-O—CH$_2$CH$_2$CH$_2$NH-immunoglobulin Fc may be formed by linking an amino group at the N-terminus of an immunoglobulin Fc region to an oxygen atom located at one end of the PEG using a linker reactive group having a structure of —CH$_2$CH$_2$CH$_2$—; and a structure in which one end of the PEG is linked to a sulfur atom located at the cysteine of a therapeutic enzyme through a thioether bond. The thioether bond described above may include the structure of

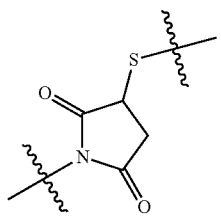

However, the non-peptide polymer is not particularly limited to the above embodiment but it is merely an embodiment.

Additionally, in the above conjugate, the reactive group of the non-peptide polymer may be linked to —NH$_2$ located at the N-terminus of an immunoglobulin Fc region, but this is merely an embodiment. Specifically, the therapeutic enzymes of the present invention may be linked to a non-peptide polymer having a reactive group through a N-terminus of the therapeutic enzyme.

As used herein, the term "N-terminus" refers to an amino end of a peptide, and for the purpose of the present invention, it refers to a position that can be linked to a non-peptide polymer. For example, although not limited thereto, the N-terminus may include not only the amino acid residue at the outermost end of a N-terminus but also all the amino acid residues near the N-terminus, and specifically, from the 1$^{st}$ amino acid residue to the 20$^{th}$ amino acid residue.

Still another aspect of the present invention provides a pharmaceutical composition for preventing or treating lysosomal storage disease (LSD) containing a therapeutic enzyme conjugate for the treatment of lysosomal storage disease.

Specifically, the enzyme is the same as described above.

Still another aspect of the present invention provides a pharmaceutical composition for preventing or treating lysosomal storage disease containing an enzyme conjugate, wherein α-galactosidase A for treating lysosomal storage disease and an immunoglobulin Fc region are linked through a non-peptide polymer linkage moiety.

Still another aspect of the present invention provides a pharmaceutical composition for preventing or treating lysosomal storage disease containing an enzyme conjugate, wherein arylsulfatase B (ARSB) for treating lysosomal storage disease and an immunoglobulin Fc region are linked through a non-peptide polymer linkage moiety.

Still another aspect of the present invention provides a pharmaceutical composition for preventing or treating lysosomal storage disease containing an enzyme conjugate, wherein iduronidase for treating lysosomal storage disease and an immunoglobulin Fc region are linked through a non-peptide polymer linkage moiety.

Still another aspect of the present invention provides a pharmaceutical composition for preventing or treating lysosomal storage disease containing an enzyme conjugate, wherein α-glucosidase for treating lysosomal storage disease and an immunoglobulin Fc region are linked through a non-peptide polymer linkage moiety.

Still another aspect of the present invention provides a pharmaceutical composition for preventing or treating lysosomal storage disease containing an enzyme conjugate, wherein imiglucerase for treating lysosomal storage disease and an immunoglobulin Fc region are linked through a non-peptide polymer linkage moiety.

The terms "lysosome", "lysosomal storage disease", "α-galactosidase A", "arylsulfatase B", "iduronidase", "α-glucosidase", "imiglucerase", "immunoglobulin Fc region", "non-peptide polymer linkage moiety", and "enzyme conjugate" are the same as described above.

As used herein, the term "prevention" refers to all activities that inhibit or delay the occurrence of lysosomal storage disease by administering the above therapeutic enzyme for the treatment of lysosomal storage disease or composition containing the therapeutic enzyme, and the term "treatment" refers to all activities that improve or advantageously change the symptoms of lysosomal storage disease by administering the therapeutic enzyme or composition containing the therapeutic enzyme.

As used herein, the term "administration" refers to the introduction of a particular substance into a patient by any appropriate method, and the administration route of the composition may be any conventional route that enables delivery of the composition to the target in vivo, for example, intraperitoneal administration, intravenous administration, intramuscular administration, subcutaneous administration, intradermal administration, oral administration, local administration, intranasal administration, intrapulmonary administration, intrarectal administration, etc.

The pharmaceutical composition of the present invention for preventing or treating lysosomal storage disease (LSD) can provide an effect of treating lysosomal storage disease by administering the lacking, deficient, or defective enzyme which becomes the cause of lysosomal storage disease to a subject with lysosomal storage disease thereby recovering the functions of lysosomal enzyme.

In an aspect, the present invention provides a pharmaceutical composition which can increase transcytosis, bioavailability, tissue distribution, and bone marrow targetability.

The pharmaceutical composition of the present invention can help the enzyme conjugate, where a therapeutic enzyme is linked to an Fc region, to easily pass through a cell membrane by binding to an FcRn receptor and can also help to more effectively arrive at the tissue from the blood vessel.

Accordingly, the pharmaceutical composition of the present invention can have enhanced transcytosis, bioavailability, tissue distribution, and bone marrow targetability thus exhibiting excellent therapeutic effect for treating lysosomal storage disease.

The pharmaceutical composition of the present invention may further contain a pharmaceutically acceptable carrier, excipient, or diluent. The pharmaceutically acceptable carrier, excipient, or diluent may be non-naturally occurring. The pharmaceutically acceptable carrier may include, for oral administration, a binder, a glidant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined to be used; and for topical administrations, a base, an excipient, a lubricant, a preserving agent, etc., but is not limited thereto.

As used herein, the term "pharmaceutically acceptable" refers to the properties of having a sufficient amount to exhibit a therapeutic effect and not causing adverse effects, and may be easily determined by a skilled person in the art based on the factors well-known in the medical field, such as the kind of disease, age, body weight, health status, sex, drug sensitivity of a patient, administration route, administration method, administration frequency, duration of treatment, a drug(s) to be mixed or administered simultaneously, etc.

The formulation type of the composition of the present invention may be prepared variously by combining with a pharmaceutically acceptable carrier described above. For example, for oral administration, the composition may be formulated into tablets, troches, capsules, elixirs, suspensions, syrups, wafers, etc. For injections, the composition may be formulated into unit-dose ampoules or multi-dose containers. The composition may also be formulated into solutions, suspensions, tablets, capsules, sustained-release formulations, etc.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preservative, etc.

Additionally, the pharmaceutical composition of the present invention may be prepared in any formulation type selected from the group consisting of tablets, pills, powders, granules, capsules, suspensions, liquid medicine for internal use, emulsions, syrups, sterile aqueous solutions, non-aqueous solvents, lyophilized formulations, and suppositories.

Additionally, the composition may be formulated into a unit dosage form suitable for the patient's body, and is specifically formulated into a preparation useful for protein drugs according to the typical method in the pharmaceutical field so as to be administered by an oral or parenteral route, such as intradermally, intravenously, intramuscularly, intraarterially, intramedullarily, intrathecally, intraventricularly, pulmonarily, transdermally, subcutaneously, intraperitoneally, intranasally, intragastrically, topically, sublingually, vaginally, or rectally, but the administration route is not limited thereto.

Additionally, the conjugate may be used by mixing with various pharmaceutically acceptable carriers approved as pharmaceutical drugs such as physiological saline or organic solvents. For increasing stability or absorptivity, carbohydrates such as glucose, sucrose, or dextrans, antioxidants such as ascorbic acid or glutathione, chelating agents, low molecular weight proteins, or other stabilizers may be used as pharmaceutical drugs.

The administration dose and frequency of the pharmaceutical composition of the present invention are determined by the type of active ingredient(s) together with various factors, such as the disease to be treated, administration route, patient's age, gender, and body weight, and severity of the disease.

The total effective dose of the composition of the present invention may be administered to a patient in a single dose or may be administered for a long period of time in multiple doses according to a fractionated treatment protocol. In the pharmaceutical composition of the present invention, the content of the active ingredient(s) may vary depending on the disease severity. Specifically, the total daily dose of the conjugate of the present invention may be about 0.0001 mg to 500 mg per 1 kg of body weight of a patient. However, the effective dose of the conjugate is determined considering various factors including patient's age, body weight, health conditions, gender, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

Still another aspect of the present invention provides a method for preventing or treating lysosomal storage disease, which includes administering a composition containing the enzyme conjugate to a subject in need thereof.

In a specific embodiment, the present invention provides a method for preventing or treating lysosomal storage disease, which includes administering a composition containing α-galactosidase A conjugate to a subject in need thereof.

Additionally, the present invention provides a method for preventing or treating lysosomal storage disease, which includes administering a composition containing arylsulfatase B (ARSB) conjugate to a subject in need thereof.

Additionally, the present invention provides a method for preventing or treating lysosomal storage disease, which includes administering a composition containing iduronidase conjugate to a subject in need thereof.

Additionally, the present invention provides a method for preventing or treating lysosomal storage disease, which includes administering a composition containing α-glucosidase conjugate to a subject in need thereof.

Additionally, the present invention provides a method for preventing or treating lysosomal storage disease, which includes administering a composition containing imiglucerase conjugate to a subject in need thereof.

The enzyme conjugates, compositions containing the enzyme conjugate, lysosomal storage disease, and prevention and treatment of lysosomal storage disease are the same as described above.

As used herein, the term "subject" refers to a subject suspected of having lysosomal storage disease, and the subject suspected of having lysosomal storage disease refers to mammals including humans, rats, cattle, etc., which have or are at the risk of developing the lysosomal storage disease, but any subject which can be treated with the conjugate of the present invention or composition containing the conjugate is included without limitation.

The method of the present invention may include administering a pharmaceutically effective amount of the pharmaceutical composition containing the conjugate. An appropriate total daily dose of the composition may be determined within the scope of correct medical judgment by a practitioner, and the composition may be administered once or several times in divided doses a day. However, for the purpose of the present invention, preferably, the specific therapeutically effective dose of the composition for any particular patient is applied differently depending on various factors including the kind and degree of responses to be achieved, specific compositions including whether other agents are occasionally used therewith, the patient's age, body weight, health conditions, gender and diet, the time and route of administration, the excretion rate of the composition, the duration of treatment, other drugs used in combination or simultaneously with the specific compositions, and similar factors well-known in the medical field.

Still another aspect of the present invention provides a composition for increasing transcytosis, bioavailability, tissue distribution, and bone marrow targetability, containing the enzyme conjugate.

In a specific embodiment, the present invention provides a composition for increasing transcytosis, bioavailability, tissue distribution, and bone marrow targetability, containing α-galactosidase A conjugate.

Additionally, the present invention provides a composition for increasing transcytosis, bioavailability, tissue distribution, and bone marrow targetability, containing arylsulfatase B (ARSB) conjugate.

Additionally, the present invention provides a composition for increasing transcytosis, bioavailability, tissue distribution, and bone marrow targetability, containing iduronidase conjugate.

Additionally, the present invention provides a composition for increasing transcytosis, bioavailability, tissue distribution, and bone marrow targetability, containing α-glucosidase conjugate.

Additionally, the present invention provides a composition for increasing transcytosis, bioavailability, tissue distribution, and bone marrow targetability, containing imiglucerase conjugate.

Still another aspect of the present invention provides a method for increasing transcytosis, bioavailability, tissue distribution, and bone marrow targetability, which includes administering the enzyme conjugate or composition containing the enzyme conjugate to a subject.

In a specific embodiment, the present invention provides a method for increasing transcytosis, bioavailability, tissue distribution, and bone marrow targetability, which includes administering an α-galactosidase A conjugate or composition containing the α-galactosidase A conjugate to a subject.

Additionally, the present invention provides a method for increasing transcytosis, bioavailability, tissue distribution, and bone marrow targetability, which includes administering an arylsulfatase B (ARSB) conjugate or composition containing the arylsulfatase B (ARSB) conjugate to a subject.

Additionally, the present invention provides a method for increasing transcytosis, bioavailability, tissue distribution, and bone marrow targetability, which includes administering an iduronidase conjugate or composition containing the iduronidase conjugate to a subject.

Additionally, the present invention provides a method for increasing transcytosis, bioavailability, tissue distribution, and bone marrow targetability, which includes administering an α-glucosidase conjugate or composition containing the α-glucosidase conjugate to a subject.

Additionally, the present invention provides a method for increasing transcytosis, bioavailability, tissue distribution, and bone marrow targetability, which includes administering an imiglucerase conjugate or composition containing the imiglucerase conjugate to a subject.

The enzyme conjugates, compositions containing the enzyme conjugate, transcytosis, bioavailability, tissue distribution, and bone marrow targetability are the same as described above.

Still another aspect of the present invention provides a use of the enzyme conjugates for preventing or treating lysosomal storage disease.

In a specific embodiment, the present invention provides a use of an α-galactosidase A conjugate for preventing or treating lysosomal storage disease.

Additionally, the present invention provides a use of an arylsulfatase B (ARSB) conjugate for preventing or treating lysosomal storage disease.

Additionally, the present invention provides a use of an iduronidase conjugate for preventing or treating lysosomal storage disease.

Additionally, the present invention provides a use of an α-glucosidase conjugate for preventing or treating lysosomal storage disease.

Additionally, the present invention provides a use of an imiglucerase conjugate for preventing or treating lysosomal storage disease.

The enzyme conjugates, lysosomal storage disease, prevention, and treatment are the same as described above.

Still another aspect of the present invention provides a use of the enzyme conjugates or a composition containing the enzyme conjugate for increasing transcytosis, bioavailability, tissue distribution, and bone marrow targetability.

In a specific embodiment, the present invention provides a use of an α-galactosidase A conjugate or composition containing the α-galactosidase A conjugate for increasing transcytosis, bioavailability, tissue distribution, and bone marrow targetability.

Additionally, the present invention provides a use of an arylsulfatase B (ARSB) conjugate or composition containing the arylsulfatase B (ARSB) conjugate for increasing transcytosis, bioavailability, tissue distribution, and bone marrow targetability.

Additionally, the present invention provides a use of an iduronidase conjugate or composition containing the iduronidase conjugate for increasing transcytosis, bioavailability, tissue distribution, and bone marrow targetability.

Additionally, the present invention provides a use of an α-glucosidase conjugate or composition containing the α-glucosidase conjugate for increasing transcytosis, bioavailability, tissue distribution, and bone marrow targetability.

Additionally, the present invention provides a use of an imiglucerase conjugate or composition containing the imiglucerase conjugate for increasing transcytosis, bioavailability, tissue distribution, and bone marrow targetability.

The enzyme conjugates, compositions containing the enzyme conjugates, transcytosis, bioavailability, tissue distribution, and bone marrow targetability are the same as described above.

Still another aspect of the present invention provides a method for preparing an enzyme conjugate represented by the following Formula 1, wherein the method includes:

(a) a step of linking a therapeutic enzyme for treating lysosomal storage disease (LSD) and a non-peptide polymer; and (b) a step of linking the linked material, where the enzyme and a non-peptide polymer are linked, and a biocompatible material capable of increasing the in vivo half-life of the enzyme;

$$X\text{-}La\text{-}F \qquad \text{[Formula 1]}$$

wherein:

X is an enzyme for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

Specifically, the enzyme is the same as described above.

In a specific embodiment, the present invention provides a method for preparing an enzyme conjugate represented by the following Formula 1, wherein the method includes:

(a) a step of linking α-galactosidase A for treating lysosomal storage disease (LSD) and a non-peptide polymer; and (b) a step of linking the linked material, where the enzyme and a non-peptide polymer are linked, and a biocompatible material capable of increasing the in vivo half-life of α-galactosidase A;

X-L$a$-F  [Formula 1]

wherein:

X is α-galactosidase A for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

In another specific embodiment, the present invention provides a method for preparing an enzyme conjugate represented by the following Formula 1, wherein the method includes:

(a) a step of linking arylsulfatase B (ARSB) for treating lysosomal storage disease (LSD) and a non-peptide polymer; and (b) a step of linking the linked material, where the enzyme and a non-peptide polymer are linked, and a biocompatible material capable of increasing the in vivo half-life of arylsulfatase B (ARSB);

X-L$a$-F  [Formula 1]

wherein:

X is arylsulfatase B (ARSB) for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

In still another specific embodiment, the present invention provides a method for preparing an enzyme conjugate represented by the following Formula 1, wherein the method includes:

(a) a step of linking iduronidase for treating lysosomal storage disease (LSD) and a non-peptide polymer; and (b) a step of linking the linked material, where the enzyme and a non-peptide polymer are linked, and a biocompatible material capable of increasing the in vivo half-life of iduronidase;

X-L$a$-F  [Formula 1]

wherein:

X is iduronidase for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

In still another specific embodiment, the present invention provides a method for preparing an enzyme conjugate represented by the following Formula 1, wherein the method includes:

(a) a step of linking α-glucosidase for treating lysosomal storage disease (LSD) and a non-peptide polymer; and (b) a step of linking the linked material, where the enzyme and a non-peptide polymer are linked, and a biocompatible material capable of increasing the in vivo half-life of α-glucosidase;

X-L$a$-F  [Formula 1]

wherein:

X is α-glucosidase for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

In still another specific embodiment, the present invention provides a method for preparing an enzyme conjugate represented by the following Formula 1, wherein the method includes:

(a) a step of linking imiglucerase for treating lysosomal storage disease (LSD) and a non-peptide polymer; and (b) a step of linking the linked material, where the enzyme and a non-peptide polymer are linked, and a biocompatible material capable of increasing the in vivo half-life of imiglucerase;

X-L$a$-F  [Formula 1]

wherein:

X is imiglucerase for treating lysosomal storage disease (LSD);

L is a non-peptide polymer;

a is 0 or natural integer, with the proviso that when a is 2 or higher, each L is independent from each other; and F is a material capable of increasing the in vivo half-life of X.

In the present invention, F may be selected from the group consisting of polymer, fatty acid, cholesterol, albumin and a fragment thereof, an albumin-binding material, a polymer of repeating units of particular amino acid sequences, an antibody, an antibody fragment, an FcRn-binding material, an in vivo connective tissue, a nucleotide, fibronectin, transferrin, a saccharide, heparin, and elastin, and more specifically, the FcRn-binding material may be an immunoglobulin Fc region, but is not limited thereto.

F may be linked to X by a covalent chemical bond or non-covalent chemical bond, and F and X may be linked through L by a covalent chemical bond, a non-covalent chemical bond, or a combination thereof.

Additionally, L may be a peptide polymer or non-peptide polymer.

When L is a peptide polymer, it can include one or more amino acids, for example, 1 to 1000 amino acids, but is not particularly limited thereto. In the present invention, various known peptide linkers may be used to link between F and X (e.g., including [GS]x linker, [GGGS]x linker, and [GGGGS]x linker, etc., wherein x is a natural number of 1 or higher), but the peptide linkers are not limited thereto.

When L is a peptide polymer, the non-peptide polymer may be one selected from the group consisting of polyethylene glycol, polypropylene glycol, an ethylene glycol/propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, and a combination thereof, and more specifically, polyethylene glycol, but is not limited thereto.

Additionally, the reactive group of the non-peptide polymer in step (a) may be one selected from the group consisting of an aldehyde group, a maleimide group, and a succinimide derivative, and more specifically, a propionaldehyde group or butyraldehyde group, or the succinimide derivative may be succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate, but is not limited thereto.

Additionally, the non-peptide polymer may have an aldehyde group as a reactive group at both ends; or have an aldehyde group and a maleimide group as a reactive group at both ends, respectively; or have an aldehyde group and a succinimide derivative as a reactive group at both ends, respectively, but the reactive group is not limited thereto.

Additionally, still another aspect of the present invention provides a method for preparing an enzyme conjugate, which further includes a step of isolating the linked material, in which a non-peptide polymer linkage moiety is linked to the N-terminus of the enzyme.

The enzyme conjugate prepared by the preparation method of the present invention, by linking a therapeutic enzyme to an Fc region, helps the enzyme conjugate to easily pass through a cell membrane by binding to the Fc region with an FcRn receptor and also help the enzyme conjugate to more effectively arrive at the tissue from the blood vessel.

All of the increased transcytosis, bioavailability, and tissue distribution can help the enzyme for treating lysosomal storage disease, contained in the enzyme conjugate, to exhibit effective therapeutic effects of the target disease while maintaining enzyme activities in the body.

Additionally, the enzyme conjugates may be those which increase the half-life of the enzymes or analogs thereof.

Hereinafter, the present invention will be described in more detail with reference to the following Examples. However, these Examples are for illustrative purposes only, and the invention is not intended to be limited by these Examples.

Example 1: Enzyme Production

For the production of long-acting enzymes, animal cells where an expression vector for animal cells was introduced were cultured and purified.

The enzymes used for the preparation of conjugates in the present invention are agalsidase β, imiglucerase, galsulfase, and laronidase.

Example 2: Preparation of Enzyme Conjugates-1

A non-peptide polymer was linked to an immunoglobulin Fc region and purified.

A non-peptide polymer was covalently linked to the N-terminus of the enzyme purified in Example 1. In particular, the non-peptide polymer was a linear polymer having an aldehyde group (—CHO) at both ends and a polyethylene glycol $(CH_2CH_2O)_n$ backbone. The size of the non-peptide polymer was determined according to the number of backbones and the aldehyde group (—CHO), which is the reactive group of the non-peptide polymer covalently binds to —$NH_2$ of the lysine residue, which is a protein-constituting element, or —$NH_2$ of the N-terminus. The aldehyde group (—CHO) of the non-peptide polymer specifically reacted with —$NH_2$ of the N-terminus under a specific reaction condition, and a non-peptide polymer enzyme which was covalently bonded in a specific manner to the N-terminus was obtained by purification.

Example 3: Preparation of Enzyme Conjugates-2

The immunoglobulin Fc region, which was linked to the non-peptide polymer purified in Example 2, was linked to enzymes purified in Example 1.

The enzymes can show differences in their activities depending on the position to which the non-peptide polymer is linked. That is, in vivo half-lives or activities of the enzymes can be enhanced depending on the site-specific binding of the enzymes. Therefore, conjugates were prepared by specifying the position to be linked to the non-peptide polymer, according to the structures of the enzymes of the present invention.

Example 3-1: Preparation of a Conjugate which Links Agalsidase and Immunoglobulin Fc by a Polyethylene Glycol A conjugate including agalsidase β was prepared as follows.

In order to link the prepared aldehyde-polyethylene glycol (Mw=10,000 Da)-aldehyde (ALD-PEG-ALD) (SUNBRIGHT DE-100AL2, NOF CORPORATION, Japan) linker to the N-terminus of agalsidase, agalsidase β and ALD-PEG-ALD were reacted in a 1:50 molar ratio (agalsidase β: 10 mg/mL) at 4° C. for about 2 hours. In particular, the reaction was performed in the presence of 100 mM sodium phosphate (pH 5.6) and 20 mM sodium cyanoborohydride was added thereto as a reducing agent. Unreacted agalsidase β and mono-linked agalsidase β were purified by the Source 15Q (GE, USA) column using a buffer containing 10 mM sodium phosphate (pH 6.0) and a sodium chloride concentration gradient.

Then, the agalsidase β linked to the purified polyethylene glycol linker was reacted with an immunoglobulin Fc fragment in a 1:10 molar ratio (total protein concentration: 10 mg/mL) at 4° C. to 8° C. for 12 hours to 16 hours. In particular, potassium phosphate (pH 6.0) was used as the reaction solution and 20 mM sodium cyanoborohydride was added thereto as a reducing agent. Upon completion of the reaction, the reaction solution was applied to the Source 15Q (GE, USA) column using a buffer containing 10 mM sodium phosphate (pH 6.0) and a sodium chloride concentration gradient and then to the Protein A (GE, USA) column using a concentration gradient of a buffer containing 20 mM Tris (pH 7.5), 5% (v/v) glycerol, sodium citrate (pH 4.0), sodium chloride, and 10% glycerol), and finally, to Superdex™ 200 (GE, USA) column using a sodium phosphate buffer containing sodium chloride, and the conjugate where an immunoglobulin Fc was covalently linked to agalsidase β by a polyethylene glycol linker was purified. Specifically, the non-peptide polymer enzyme purified in Example 2 and the immunoglobulin Fc region were covalently bonded through the unreacted aldehyde group (—CHO) on the other end of the non-peptide polymer and the $NH_2$ of the N-terminus, and purified after the covalent bonding, thereby completing the preparation of the enzyme conjugate.

The finally prepared agalsidase β-polyethylene glycol linker-immunoglobulin Fc conjugate was in a form where agalsidase were linked to one chain of the immunoglobulin Fc, which consists of two chains, by a polyethylene glycol linker.

Example 3-2: Preparation of a Conjugate which Links Imiglucerase and Immunoglobulin Fc by a Polyethylene Glycol A conjugate including imiglucerase was prepared as follows.

In order to link an aldehyde-polyethylene glycol (Mw=10,000 Da)-aldehyde (ALD-PEG-ALD) (SUNBRIGHT DE-100AL2, NOF CORPORATION, Japan) linker to the N-terminus of imiglucerase, imiglucerase and ALD-PEG-ALD were reacted in a 1:50 molar ratio (concentration of imiglucerase: 1 mg/mL) at 25° C. for about 1 hour. In particular, the reaction was performed in the presence of 100 mM potassium phosphate (pH 6.0), and 20 mM sodium cyanoborohydride was added thereto as a reducing agent. Unreacted imiglucerase and mono-linked imiglucerase were purified by the Source 15S (GE, USA) column using a buffer containing 20 mM sodium phosphate (pH 6.0) and 2.5% (v/v) glycerol and a sodium chloride concentration gradient.

Then, the imiglucerase linked to the purified polyethylene glycol linker was reacted with an immunoglobulin Fc fragment in a 1:50 molar ratio (total protein concentration: 40 mg/mL) at 4° C. to 8° C. for 12 hours to 16 hours. In particular, 100 mM potassium phosphate (pH 6.0) was used as the reaction solution and 20 mM sodium cyanoborohydride was added thereto as a reducing agent. Upon completion of the reaction, the reaction solution was applied to the Source 15S (GE, USA) column using a buffer containing 10 mM sodium citrate (pH 5.0) and a sodium chloride concentration gradient and to the Protein A (GE, USA) column using a concentration gradient of a buffer containing 20 mM Tris (pH 7.5), 5% (v/v) glycerol, 100 mM sodium citrate (pH 3.7), sodium chloride, 10% glycerol), and finally, to Superdex™ 200 (GE, USA) column using a 50 mM sodium citrate buffer (pH 6.1) containing sodium chloride, and the conjugate where an immunoglobulin Fc was covalently linked to imiglucerase by a polyethylene glycol linker was purified.

Specifically, the purified non-peptide polymer enzyme and the immunoglobulin Fc region were covalently bonded through the unreacted aldehyde group (—CHO) on the other end of the non-peptide polymer and the $NH_2$ of the N-terminus, and purified after the covalent bonding, thereby completing the preparation of the enzyme conjugate.

The finally prepared imiglucerase-polyethylene glycol linker-immunoglobulin Fc conjugate was in a form where imiglucerase monomers were linked to one chain of the immunoglobulin Fc, which consists of two chains, by a polyethylene glycol linker.

Example 3-3: Preparation of a Conjugate which Links Galsulfase and Immunoglobulin Fc by a Polyethylene Glycol A conjugate including galsulfase was prepared as follows.
In order to link an aldehyde-polyethyleneglycol-aldehdye (Mw=10 kDa) (SUNBRIGHT DE-100AL2, NOF CORPORATION, Japan) linker to the N-terminus of galsulfase, galsulfase and ALD-PEG-ALD were reacted in a 1:20 molar ratio (concentration of galsulfase: 1 mg/mL) at 25° C. for about 2 hours. In particular, the reaction was performed in the presence of 12 mM sodium phosphate and 150 mM sodium chloride (pH 5.8), and 20 mM sodium cyanoborohydride was added thereto as a reducing agent. Unreacted galsulfase and mono-PEG galsulfase were purified by the Source 15Q (GE, USA) column using 20 mM Tris (pH 7.0) buffer and a sodium chloride concentration gradient and the Source ISO (GE, USA) column equilibrated with 1.8 M ammonium sulfate.

Then, the galsulfase linked to the purified polyethylene glycol linker was reacted with an immunoglobulin Fc fragment in a 1:20 molar ratio (total protein concentration: 50 mg/mL) at 4° C. to 8° C. for 12 hours to 16 hours. In particular, potassium phosphate (pH 6.0) was used as the reaction solution and 20 mM sodium cyanoborohydride was added thereto as a reducing agent. Upon completion of the reaction, the reaction solution was applied to the Source 15 Q (GE, USA) column using 20 mM Tris buffer (pH 7.0) and a sodium chloride concentration gradient, and then to the Protein A (GE, USA) column using a concentration of a buffer containing 20 mM Tris (pH 7.0), 5% (v/v) glycerol, sodium citrate (pH 3.0), and 10% glycerol), and finally, to Source ISO (GE, USA) column equilibrated with 1.8 M ammonium sulfate, and the conjugate where an immunoglobulin Fc was covalently linked to galsulfase by a polyethylene glycol linker was purified.

Specifically, the purified non-peptide polymer enzyme and the immunoglobulin Fc region were covalently bonded through the unreacted aldehyde group (—CHO) on the other end of the non-peptide polymer and the $NH_2$ of the N-terminus, and purified after the covalent bonding, thereby completing the preparation of the enzyme conjugate.

The finally prepared galsulfase-polyethylene glycol linker-immunoglobulin Fc conjugate was in a form where galsulfase monomers were linked to one chain of the immunoglobulin Fc, which consists of two chains, by a polyethylene glycol linker.

Example 3-4: Preparation of a Conjugate which Links Laronidase and Immunoglobulin Fc by a Polyethylene Glycol A conjugate including laronidase was prepared as follows.
In order to link an aldehyde-polyethylene glycol (Mw=10 kDa)-aldehyde (ALD-PEG-ALD) (SUNBRIGHT DE-100AL2, NOF CORPORATION, Japan) linker to the N-terminus of laronidase, laronidase and ALD-PEG-ALD were reacted in a 1:100 molar ratio (concentration of laronidase: 0.58 mg/mL) at 4° C. to 8° C. for about 16 hours. In particular, the reaction was performed in the presence of 100 mM potassium phosphate (pH 6.0) and 10 mM sodium cyanoborohydride was added thereto as a reducing agent. The mono-linked laronidase with polyethylene glycol linker were purified by the Source 15S (GE, USA) column using potassium phosphate (pH 6.0) and a sodium chloride concentration gradient and the Source 15ISO (GE, USA) column using potassium phosphate (pH 6.0) and an ammomium sulfate concentration gradient.

Then, the purified laronidase linked to the polyethylene glycol linker was reacted with an immunoglobulin Fc fragment in a 1:10 molar ratio (total protein concentration: 20 mg/mL) at 4° C. to 8° C. for 14 hours. In particular, 100 mM potassium phosphate (pH 6.0) was used as the reaction solution and 10 mM sodium cyanoborohydride was added thereto as a reducing agent. Upon completion of the reaction, the reaction solution was applied to the Source 15S (GE, USA) column using a potassium phosphate (pH 6.0) buffer and a sodium chloride concentration gradient, and finally, to the Protein A (GE, USA) column using a concentration gradient of a buffer containing 20 mM Tris (pH 7.5), 5% (v/v) glycerol and 100 mM citric acid monohydrate (pH 3.7), and 10% glycerol and 100 mM citric acid monohydrate (pH4.0), and 10% glycerol, and the conjugate where an immunoglobulin Fc was covalently linked to laronidase by a polyethylene glycol linker was purified.

Specifically, the purified non-peptide polymer enzyme and the immunoglobulin Fc region were covalently bonded through the unreacted aldehyde group (—CHO) on the other end of the non-peptide polymer and the $NH_2$ of the N-terminus, and purified after the covalent bonding, thereby completing the preparation of the enzyme conjugate.

The finally prepared laronidase-polyethylene linker-immunoglobulin Fc conjugate was in a form where laronidase monomers were linked to one chain of the immunoglobulin Fc, which consists of two chains, by a polyethylene glycol linker.

Example 4: Pharmacokinetic Experiment on Enzyme Conjugates

The present inventors attempted to confirm the effects of conjugates by examining the pharmacokinetics of the enzyme conjugates prepared in Examples.

Example 4-1: Confirmation of Pharmacokinetics (PK) of Long-Acting Imiglucerase Conjugate The present inventors confirmed the PK activities of the long-acting imiglucerase conjugate prepared in Examples.

The blood stability of imiglucerase (control group) and the long-acting imiglucerase conjugate prepared in Examples in three ICR mice from each group at the time of blood collection and their pharmacokinetic coefficients were compared.

Specifically, the control group and test groups were intravenously injected in an amount of 1.5 mg/kg per mouse based on imiglucerase, respectively. Blood samples were collected from the mice in the groups with intravenous injection at 0, 2, 5, 10, 20, and 60 minutes after the injection, and the amount of proteins in the blood serum was measured by ELISA assay using antibody to imiglucerase.

As a result of the PK analysis, the long-acting imiglucerase conjugate was shown to increase both in blood half-life and area under curve (AUC) compared to that of control group, and in particular, the blood half-life showed at least a 4-fold increase. The AUC represents the degree of in vivo exposure to drug molecules.

Example 4-2: Confirmation of PK of Long-Acting Agalsidase Conjugate

The blood stability of agalsidase β (control group) and the long-acting agalsidase β conjugate prepared in Examples in one or three ICR mice from each group at the time of blood collection and their pharmacokinetic coefficients were compared.

Specifically, the control group and test groups were intravenously and subcutaneously injected in an amount of 1.0 mg/kg per mouse based on agalsidase β, respectively. Blood samples were collected from the mice in the groups with intravenous and subcutaneous injections at 0, 0.25, 0.5, 0.75, 1, 1.5, 2, 3, 4, 8, 24, and 48 hours after the injections. For the mice in the test groups with intravenous injection, blood samples were collected at 0, 0.25, 0.5, 1, 2, 4, 8, 24, 48, 72, 96, 120, 144, and 168 hours after the injection, whereas for the mice in the test groups with subcutaneous injection, blood samples were collected at 0, 1, 2, 4, 8, 24, 48, 72, 96, 120, 144, and 168 hours after the injection, respectively. The amount of proteins in the blood serum was measured by ELISA assay using antibody to agalsidase (3.

As a result, the long-acting agalsidase β conjugate was shown to increase in all of blood half-life, $C_{max}$, and AUC compared to that of control group. Additionally, the bioavailability (BA) of the long-acting agalsidase β conjugate was shown to be 58.2%, which was about 18-fold higher compared to that of agalsidase β (3.3%) thus confirming the excellent BA of the long-acting agalsidase β conjugate (FIG. 1).

$C_{max}$ represents the maximum drug concentration, AUC represents the degree of in vivo exposure to drug molecules, and BA represents the rate of utilization in vivo.

The present inventors attempted to confirm the in vitro activities for each of the conjugates prepared above as follows.

Example 5: Confirmation of the Activity of an Agalsidase Conjugate

Example 5-1: In Vitro Enzyme Activity of Long-Acting Agalsidase Conjugate

The present inventors performed the measurements of in vitro enzyme activity for measuring the changes in the enzyme activity of agalsidase β according to the preparation of a long-acting agalsidase conjugate.

Specifically, 4-nitrophenyl-α-D-galactopyranoside, which is known as a substrate for enzyme, was reacted with agalsidase β and a long-acting agalsidase β conjugate at 37° C. for 20 minutes, and the enzyme activity for the corresponding material was measured by measuring the absorbance of 4-nitrophenol, the final product thereof.

As a result, it was confirmed that the enzyme activity (specific activity) of agalsidase β and the long-acting agalsidase β conjugate were 63.6 μmol/min/μg and 56.3 μmol/min/μg, respectively. Conclusively, the enzyme activity of the long-acting conjugate of agalsidase compared to that of free agalsidase β was 88.6%, thus confirming that the decrease in enzyme activity according to the preparation of the long-acting agalsidase conjugate was negligible (FIG. 2).

Example 5-2: Intracellular Uptake Activity of a Long-Acting Agalsidase Conjugate Since agalsidase β acts after being absorbed into cells by mannose-6-phosphate receptor (M6PR), it was examined whether the preparation of a long-acting agalsidase β conjugate can affect the activity of cellular uptake of the enzyme as follows.

Specifically, CCD986SK cells (human skin fibroblasts), which are known to express M6PR, were first reacted with agalsidase β and a long-acting agalsidase β conjugate, respectively, and intracellular uptake was induced at 37° C. Twenty four hours thereafter, agalsidase β and the long-acting agalsidase β conjugate present in the cells were confirmed by an enzyme activity measurement assay.

As a result, it was confirmed that the intracellular uptake activity of the long-acting agalsidase β conjugate ($K_{uptake}$=29.3 nM) was about 47% relative to that of agalsidase β ($K_{uptake}$=13.7 nM). The decrease in the binding to M6PR and intracellular absorption activity (vs. agalsidase β) was due to the steric hindrance of the long-acting conjugate, and the decrease can be compensated by the PK improved by the conjugation due to the preparation of the long-acting conjugate (FIG. 3).

Example 5-3: Confirmation of Binding Affinity of Long-Acting Agalsidase Conjugate to M6P Receptor For the confirmation of binding affinity of agalsidase β and the long-acting agalsidase β conjugate to mannose phosphate 6 receptor (M6PR), an analysis was performed using the surface plasmon resonance (BIACORE T200, GE healthcare).

Specifically, the M6PR was immobilized to a CM5 chip by amine coupling. Then, agalsidase β was diluted with HBS-EP buffer to a concentration of 200 nM to 12.5 nM, linked to the chip where the M6PR was immobilized for 10 minutes, dissociated for 6 minutes, and the binding affinity was calculated using the BIAevaluation software. The relative binding affinity of the long-acting agalsidase β conjugate was digitized by comparing with that of agalsidase β.

As a result, it was confirmed that the receptor binding affinity of the long-acting agalsidase β conjugate was about 68% of that of agalsidase β (Table 1). It appears that the relatively low binding affinity of the long-acting agalsidase β conjugate to M6PR was due to the the same reason that a physiologically active polypeptide conventionally shows a decrease in its binding affinity to its receptors when it forms a fusion protein with an Fc region. To help the understanding of the present invention, rather than intending to be strictly bound to a particular theory of action of the present invention, the low binding affinity may be because the association rate constant ($k_a$) to the receptors was decreased due to steric hindrance on the agalsidase region as the immunoglobulin Fc and agalsidase β were covalently bonded. In a case of a long-acting conjugate, which was once linked, there was no difference in dissociation rate constant ($k_d$) compared to that of the free agalsidase, which did not form a conjugate.

TABLE 1

| Name of Material | ka (1/Ms, ×10$^5$) | ka (1/s, ×10$^{-3}$) | $K_D$ (nM) |
| --- | --- | --- | --- |
| Agalsidase beta | 1.35 ± 0.25 (100%) | 2.73 ± 0.86 (100%) | 20.0 ± 3.58 (100%) |
| Long-acting agalsidase beta conjugate | 0.80 ± 0.02 (70.4%) | 2.77 ± 0.86 (101%) | 29.6 ± 3.66 (67.6%) |

The results of confirming the activity of the long-acting agalsidase β conjugate of the present invention are summarized below.

TABLE 2

| In vitro Activity (vs. 1$^{st}$ ERT) | | | In vivo Activity (vs. 1$^{st}$ ERT) PK | |
| --- | --- | --- | --- | --- |
| Enzyme activity | Binding affinity to M6PR | Intracellular uptake | $t_{1/2}$ | AUC |
| 87% | 68% | 47% | 125 fold | 18 fold |

Example 6: Confirmation of the Activity of Imiglucerase Conjugate

Example 6-1: In Vitro Enzyme Activity of the Long-Acting Imiglucerase Conjugate

The in vitro enzyme activities of imiglucerase (control group) and the long-acting imiglucerase conjugate (test group) prepared above were compared.

Specifically, for the measurement of enzyme activities, p-Nitrophenyl β-D-glucopyranoside was used as a substrate, and the amount of products produced per unit time was calculated by quantitating the amount of p-Nitrophenol (pNP) produced according to enzyme activity and the absolute enzyme activity (specific activity) was obtained. The control group and the test group were treated in a concentration of 0.1 μg/mL based on imiglucerase. The substrate was treated with 20, 16, 12, 8, 4, 2, 1, and 0 mM, respectively, and reacted at 37° C. for 45 minutes. The amount of the finally produced pNP was quantiated by measuring the absorbance at 405 nm. The values of μmole/min/mg were calculated using the concentration, reaction volume, and reaction time of the quantitated pNP. Finally, the value of $V_{max}$ (μmole/min/mg=U/mg), which is the enzyme activity, was finally calculated by substituting the value x in Michaelis-Menten equation with the concentration of a substrate and substituting the y value with the value calculated above.

As a result, it was confirmed that the enzyme activities of imiglucerase and the long-acting imiglucerase conjugate were 48.5 U/mg and 45.2 U/mg, respectively. Conclusively, the enzyme activity of the long-acting imiglucerase conjugate compared to that of the control group was 93% thus confirming that there was no decrease in the enzyme activity by the conjugation to an immunoglobulin Fc (FIG. 4).

Example 6-2: Confirmation of the Binding Affinity of the Long-Acting Imiglucerase Conjugate to M6P Receptors For the confirmation of binding affinity to M6PR, an analysis was performed by the surface plasmon resonance (SPR, BIACORE T200) using imiglucerase (control group) and the long-acting imiglucerase conjugate (test group) prepared above. M6PR was purchased from R&D Systems Inc. After immobilizing M6PR to a CM5 chip by amine coupling, the binding affinities were confirmed by flowing in a concentration of 100 nM to 6.24 nM for the control group and in a concentration of 200 nM to 12.5 nM for the test group.

The HBS-EP buffer (pH 7.5) was used as a running buffer. All test materials were diluted with the running buffer and induced to conjugate and the dissociation was performed using the running buffer. The test materials were flowed into the M6PR, which was immobilized to the chip, for 10 minutes and then subjected to a dissociation process for 6 minutes.

Then, for the conjugation of the control group or test group in a different concentration, 5 mM NaOH/50 mM NaCl was flowed for about 30 seconds into the conjugate, which was conjugated to the M6PR. The binding affinities between M6PR and imiglucerase or the long-acting imiglucerase conjugate were analyzed using the BIAevaluation program. The association rate constant ($K_a$), dissociation rate constant ($K_d$), and affinity constant ($K_D$) values were calculated using the 1:1 Langmuir binding model.

As a result, it was confirmed that there was no big difference in the dissociation constant by the conjugation to an immunoglobulin Fc, but there was a difference in the coupling constant. Accordingly, the binding affinity of the test group showed a decrease of about 22% compared to that of the control group (Table 3). It appears that the relatively low binding affinity of the long-acting imiglucerase conjugate to M6PR was due to the same reason that a physiologically active polypeptide conventionally shows a decrease in its binding affinity to its receptors when it forms a fusion protein with an Fc region. To help the understanding of the present invention, rather than intending to be strictly bound to a particular theory of action of the present invention, the low binding affinity may be because the association rate constant ($k_a$) to the receptors was decreased due to steric hindrance on the imiglucerase region as the immunoglobulin Fc and imiglucerase were covalently bonded. In a case of a long-acting conjugate, which was once linked, there was no difference in dissociation rate constant ($k_d$) compared to that of the free imiglucerase, which did not form a conjugate (Table 3).

TABLE 3

| Test Materials | $K_a$ (1/Ms, ×$10^5$) | $K_d$ (1/s, ×$10^{-3}$) | $K_D$ (nM) |
|---|---|---|---|
| Imiglucerase | 2.32 ± 0.68 | 3.87 ± 0.46 | 17.3 ± 0.35 |
| Long-acting imiglucerase conjugate | 0.49 ± 0.00 | 3.90 ± 0.16 | 79.6 ± 0.33 |

The results of confirming the activity of the long-acting imiglucerase conjugate of the present invention are summarized below.

TABLE 4

| In vitro Activity (vs. $1^{st}$ ERT) | |
|---|---|
| Enzyme activity | Binding affinity to M6PR |
| 93% | 22% |

Example 7: Confirmation of the Activity of the Enzyme Conjugate for Galsulfase

Example 7-1: In Vitro Enzyme Activity of the Long-Acting Galsulfase Conjugate

The in vitro enzyme activities of galsulfase (control group) and the long-acting galsulfase conjugate (test group) prepared above were compared.

Specifically, for the measurement of enzyme activities, 4-methylumbelliferyl sulfate (4-MUS) was used as a substrate, and the enzyme activity for a subject material was measured by measuring the fluorescence of the 4-methylumbelliferone (4-MU), which was generated by the enzyme reaction performed at 37° C. for 20 minutes.

As a result, it was confirmed that the enzyme activities of galsulfase and the long-acting conjugate of galsulfase were 72.3 μ mole/min/mg and 81.3 μ mole/min/mg, respectively. Conclusively, the enzyme activity of the long-acting conjugate of galsulfase compared to that of the control group was 112% thus confirming that there was no decrease in the enzyme activity by the conjugation to an immunoglobulin Fc (FIG. 5).

Example 7-2: Confirmation of the Binding Affinity of the Long-Acting Galsulfase Conjugate to M6P Receptors For the confirmation of binding affinity to M6PR, an analysis was performed by the surface plasmon resonance (SPR, BIACORE T200) using galsulfase (control group) and the long-acting galsulfase conjugate (test group) prepared above.

Specifically, M6PR was purchased from R&D Systems Inc. After immobilizing M6PR to a CM5 chip by amine coupling, the binding affinities of test materials were confirmed by flowing in a concentration of 100 nM to 6.24 nM. The HBS-EP buffer (pH 7.5) was used as a running buffer. All test materials were diluted with the running buffer and induced to conjugate and the dissociation was performed using the running buffer. The test materials were flowed into the M6PR, which was immobilized to the chip, for 10 minutes and then subjected to a dissociation process for 6 minutes.

Then, for the conjugation of the control group or test group in a different concentration, 5 mM NaOH/50 mM NaCl was flowed into the conjugate, which was conjugated to the M6PR for about 30 seconds. The binding affinities between M6PR and galsulfase or the long-acting galsulfase conjugate were analyzed using the BIAevaluation program. The association rate constant ($K_a$), dissociation rate constant ($K_d$), and affinity constant ($K_D$) values were calculated using the 1:1 Langmuir binding model.

As a result, it was confirmed that there was no big difference in the dissociation constant by the conjugation to an immunoglobulin Fc, but there was a difference in the coupling constant. Accordingly, the binding affinity of the test group showed a decrease of about 25% compared to that of the control group (Table 5). It appears that the relatively low binding affinity of the long-acting galsulfase conjugate to M6PR was due to the same reason that a physiologically active polypeptide conventionally shows a decrease in its binding affinity to its receptors when it forms a fusion protein with an Fc region. To help the understanding of the present invention, rather than intending to be strictly bound to a particular theory of action of the present invention, the low binding affinity may be because the association rate constant ($k_a$) to the receptors was decreased due to steric hindrance on the galsulfase region as the immunoglobulin Fc and galsulfase were covalently bonded. In a case of a long-acting conjugate, which was once linked, there was no difference in dissociation rate constant ($k_d$) compared to that of the free imiglucerase, which did not form a conjugate (Table 5).

TABLE 5

| Test Materials | $K_a$ (1/Ms, ×$10^5$) | $K_d$ (1/s, ×$10^{-3}$) | $K_D$ (nM) |
|---|---|---|---|
| Galsulfase | 34.9 ± 3.7 | 1.30 ± 0.00 | 0.38 ± 0.04 |
| Long-acting galsulfase conjugate | 8.32 ± 0.80 | 1.22 ± 0.01 | 1.48 ± 0.15 |

The results of confirming the activity of the long-acting galsulfase conjugate galsulfase of the present invention are summarized below.

TABLE 6

| In vitro activity (vs. $1^{st}$ ERT) | |
|---|---|
| Enzyme activity | Binding affinity to M6PR |
| 112% | 25% |

Example 8: Confirmation of the Activity of Iduronidase Conjugate

Example 8-1: In Vitro Enzyme Activity of the Long-Acting Iduronidase Conjugate

For the measurement of the changes in enzyme activity according to the preparation of the long-acting iduronidase conjugate, in vitro enzyme activities were measured.

Specifically, 4-methylumbelliferyl alpha-L-iduronide (4-MUI), which is known as a substrate for enzymes, was reacted with iduronidase and a long-acting iduronidase conjugate at 37° C. for 30 minutes. The enzyme activity for the corresponding material was measured by measuring the fluorescence with respect to the 4-methylumbelliferone (4MU), which is the final product thereof.

As a result, it was confirmed that the enzyme activities (specific activities) of iduronidase and the long-acting iduronidase conjugate were 127.5±15.8 µmol/min/mg and 132.2±24.3 µmol/min/mg, respectively. Conclusively, the enzyme activity of the long-acting iduronidase conjugate compared to that of iduronidase was 105.7±32.2%, thus confirming that there was no decrease in enzyme activity according to the preparation of the long-acting conjugate (FIG. 6).

Example 8-2: Confirmation of the Binding Affinity of the Long-Acting Iduronidase Conjugate to M6P Receptors For the confirmation of binding affinity to M6PR, an analysis was performed by the surface plasmon resonance (SPR, BIACORE T200) using iduronidase (control group) and the long-acting iduronidase conjugate (test group) prepared above.

Specifically, M6PR was purchased from R&D Systems Inc. After immobilizing M6PR to a CM5 chip by amine coupling, the binding affinities of test materials were confirmed by flowing in a concentration of 50 nM to 3.125 nM for the control group and in a concentration of 100 nM to 6.25 nM for the test group.

The HBS-EP buffer (pH 7.5) was used as a running buffer. All test materials were diluted with the running buffer and induced to conjugate and the dissociation was performed using the running buffer. The test materials were flowed into the M6PR, which was immobilized to the chip, for 10 minutes and then subjected to a dissociation process for 6 minutes. Then, for the conjugation of the control group or test group in a different concentration, 5 mM NaOH/50 mM NaCl was flowed for about 30 seconds into the conjugate, which was conjugated to the M6PR. The binding affinities between M6PR and iduronidase or the long-acting iduronidase conjugate were analyzed using the BIAevaluation program. The association rate constant ($K_a$), dissociation rate constant ($K_d$), and affinity constant ($K_D$) values were calculated using the 1:1 Langmuir binding model.

As a result, it was confirmed that there were differences both in the dissociation constant and in the coupling constant by the conjugation to an immunoglobulin Fc. Accordingly, the binding affinity of the test group showed a decrease of about 13% compared to that of the control group.

It appears that the relatively low binding affinity of the long-acting iduronidase conjugate to M6PR was due to the same reason that a physiologically active polypeptide conventionally shows a decrease in its binding affinity to its receptors when it forms a fusion protein with an Fc region. To help the understanding of the present invention, rather than intending to be strictly bound to a particular theory of action of the present invention, the low binding affinity may be because the association rate constant ($k_a$) to the receptors was decreased due to steric hindrance on the iduronidase region as the immunoglobulin Fc and iduronidase were covalently bonded (Table 7).

TABLE 7

| Test Materials | $K_a$ (1/Ms, ×10$^5$) | $K_d$ (1/s, ×10$^{-3}$) | $K_D$ (nM) |
| --- | --- | --- | --- |
| Iduronidase | 169.3 ± 22.1 | 5.65 ± 4.50 | 0.59 ± 0.34 |
| Long-acting iduronidase conjugate | 4.74 ± 0.37 | 2.23 ± 0.14 | 4.72 ± 0.40 |

The results of confirming the activity of the long-acting iduronidase conjugate of the present invention are summarized below.

TABLE 8

| In vitro Activity (vs. 1$^{st}$ ERT) ||
| --- | --- |
| Enzyme activity | Binding affinity to M6PR |
| 114% | 13% |

The above results suggest that the enzyme conjugates of the present invention have excellent transcytosis, in vivo bioavailability (BA), tissue distribution, and bone marrow targetability compared to other therapeutic enzymes and can thus be used as a significant therapeutic agent for the treatment of lysosomal storage disease (LSD).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. An enzyme conjugate, wherein a therapeutic enzyme for treating lysosomal storage disease (LSD) and an immunoglobulin Fc region are linked through a non-peptide polymer linkage moiety,
   wherein the non-peptide polymer linkage moiety is linked to the N-terminus of the immunoglobulin Fc region; and
   wherein the enzyme conjugate has increased bioavailability (BA) compared to the enzyme to which the immunoglobulin Fc region is not linked.

2. The enzyme conjugate of claim 1, wherein the enzyme is selected from the group consisting of β-glucosidase, β-galactosidase, galactose-6-sulfatase, acid ceramidase, acid sphingomyelinase, galactocerebrosidase, arylsulfatase A, β-hexosaminidase A, β-hexosaminidase B, heparan N-sulfatase, α-D-mannosidase, β-glucuronidase, N-acetylgalactosamine-6 sulfatase, lysosomal acid lipase, α-N-acetyl-D-glucosaminidase (NAGLU), glucocerebrosidase, butyrylcholinesterase, chitinase, glutamate decarboxylase, lipase, uricase, platelet-activating factor acetylhydrolase, neutral endopeptidase, myeloperoxidase, acetyl-CoA-glucosaminide N-acetyltransferase, N-acetylglucosamine-6-sulfatase, galactosamine 6-sulfatase (GALNS), hyaluronidase, α-fucosidase, β-mannosidase, α-neuraminidase (sialidase), N-acetyl-glucosamine-1-phosphotransferase, mucolipin-1, α-N-acetyl-galactosaminidase, N-aspartyl-β- glucosaminidase, LAMP-2 (Lysosome-associated membrane protein 2), cystinosin, sialin, ceramidase, acid-β-glucosidase, galactosyl ceramidase, NPC1 (Niemann-Pick disease, type C1), cathepsin A, SUMF-1 (Sulfatase-modifying factor 1), lysosomal acid lipase (LIPA), and andtripeptidyl peptidase 1.

3. The enzyme conjugate of claim 1, wherein the enzyme is selected from the group consisting of α-galactosidase A, arylsulfatase B (ARSB), iduronidase, α-glucosidase, and imiglucerase.

4. The enzyme conjugate according to claim 1, wherein the lysosomal storage disease is selected from the group consisting of mucopolysaccharidosis (MPS), glycogen storage disease, and sphingolipidosis.

5. The enzyme conjugate of claim 4, wherein the mucopolysaccharidosis (MPS) is selected from the group consisting of mucopolysaccharidosis I (MPS I) and mucopolysaccharidosis VI (MPS VI); wherein the glycogen storage disease is Pompe disease; or wherein the sphingolipidosis is selected from the group consisting of Fabry disease and Gaucher's disease.

6. The enzyme conjugate according to claim 1, wherein the enzyme conjugate has increased transcytosis and bioavailability (BA) compared to the enzyme to which the immunoglobulin Fc region is not linked.

7. The enzyme conjugate of claim 6, wherein the transcytosis is mediated by binding between the immunoglobulin Fc region and a neonatal Fc receptor (FcRn).

8. The enzyme conjugate according to claim 1, wherein the enzyme conjugate has an increased tissue distribution compared to the enzyme; to which the immunoglobulin Fc region is not linked.

9. The enzyme conjugate of claim 8, wherein the enzyme conjugate has an increased bone marrow targetability compared to the enzyme to which the immunoglobulin Fc region is not linked.

10. The enzyme conjugate according to claim 1, wherein the immunoglobulin Fc region is aglycosylated; or
wherein the immunoglobulin Fc region comprises one to four domains selected from the group consisting of CH1, CH2, CH3, and CH4 domains; or
wherein the immunoglobulin Fc region further comprises a hinge region; or
wherein the immunoglobulin Fc region is an immunoglobulin Fc fragment derived from IgG, IgA, IgD, IgE, or IgM; or
wherein each domain of the immunoglobulin Fc region is a hybrid of domains having different origins derived from the immunoglobulins selected from the group consisting of IgG, IgA, IgD, IgE, and IgM; or
wherein the immunoglobulin Fc region is a dimer or multimer consisting of single-chain immunoglobulins composed of domains of the same origin; or
wherein the immunoglobulin Fc region is an IgG4 Fc fragment; or
wherein the immunoglobulin Fc region is a human aglycosylated IgG4 Fc fragment.

11. The enzyme conjugate according to claim 1, wherein the non-peptide polymer linkage moiety is linked to the N-terminus of the enzyme.

12. A pharmaceutical composition comprising the enzyme conjugate of claim 1.

13. The pharmaceutical composition of claim 12, wherein the enzyme of the enzyme conjugate is selected from the group consisting of α-galactosidase A, arylsulfatase B (ARSB), iduronidase, α-glucosidase and imiglucerase.

14. The pharmaceutical composition according to claim 12, wherein the pharmaceutical composition increases transcytosis, bioavailability, tissue distribution, and bone marrow targetability.

15. A method for preparing an enzyme conjugate of claim 1, comprising:
(a) a step of linking a therapeutic enzyme for treating lysosomal storage disease (LSD) and a non-peptide polymer to prepare a linked material wherein the therapeutic enzyme and the non-peptide polymer are linked; and
(b) a step of linking the linked material from step (a) to the N-terminus of an immunoglobulin Fc region.

16. The method of claim 15, wherein the therapeutic enzyme is selected from the group consisting of β-glucosidase, β-galactosidase, galactose-6-sulfatase, acid ceramidase, acid sphingomyelinase, galactocerebrosidase, arylsulfatase A, β-hexosaminidase A, β-hexosaminidase B, heparan N-sulfatase, α-D-mannosidase, β-glucuronidase, N-acetylgalactosamine-6 sulfatase, lysosomal acid lipase, α-N-acetyl-D-glucosaminidase (NAGLU), glucocerebrosidase, butyrylcholinesterase, chitinase, glutamate decarboxylase, lipase, uricase, platelet-activating factor acetylhydrolase, neutral endopeptidase, myeloperoxidase, acetyl-CoA-glucosaminide N-acetyltransferase, N-acetylglucosamine-6-sulfatase, galactosamine 6-sulfatase (GALNS), hyaluronidase, α-fucosidase, β-mannosidase, α-neuraminidase (sialidase), N-acetyl-glucosamine-1-phosphotransferase, mucolipin-1, α-N-acetyl-galactosaminidase, N-aspartyl-β-glucosaminidase, LAMP-2 (Lysosome-associated membrane protein 2), cystinosin, sialin, ceramidase, acid-β-glucosidase, galactosylceramidase, NPC1 (Niemann-Pick disease, type C1), cathepsin A, SUMF-1 (Sulfatase-modifying factor 1), lysosomal acid lipase (LIPA), and tripeptidyl peptidase 1.

17. The method of claim 15, wherein the enzyme conjugate is represented by the following Formula 1, X-L$a$-F　　　　　[Formula 1]

wherein:
X is the therapeutic enzyme selected from the group consisting of α-galactosidase A, arylsulfatase B (ARSB), iduronidase, α-glucosidase, and imiglucerase;
L is a non-peptide polymer;
a is 0 or natural integer, with the proviso that when a is 2 or higher, each L is independent from each other; and
F is the immunoglobulin Fc region.

18. The method of claim 15, wherein the therapeutic enzyme is selected from the group consisting of α-galactosidase A, arylsulfatase B (ARSB), iduronidase, α-glucosidase and imiglucerase.

19. The method according to claim 15, wherein the non-peptide polymer is selected from the group consisting of polyethylene glycol, polypropylene glycol, an ethylene glycol/propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, and a combination thereof; or
wherein the non-peptide polymer of step (a) has a reactive group selected from the group consisting of an aldehyde group, a maleimide group, and a succinimide group; or
wherein the non-peptide polymer of step (a) has an aldehyde group as a reactive group at both ends; or
wherein the non-peptide polymer of step (a) has an aldehyde group and a maleimide group as a reactive group at both ends, respectively; or wherein the non-peptide polymer of step (a) has an aldehyde group and a succinimide group as a reactive group at both ends, respectively.

20. The method of claim 19, wherein the aldehyde group is a propionaldehyde group or butyraldehyde group; or wherein the succinimide group is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

21. The method according to claim 15, further comprising a step of isolating the linked material prepared in step (a), wherein the non-peptide polymer linkage moiety is linked to the N-terminus of the therapeutic enzyme.

22. A method for increasing the transcytosis of an enzyme in a subject in need thereof, comprising administering the enzyme conjugate of claim 1 to the subject.

23. A method for increasing the tissue distribution of an enzyme in a subject in need thereof, comprising administering the enzyme conjugate of claim 1 to the subject.

24. The method of claim 22, wherein the enzyme is selected from the group consisting of α-galactosidase A, arylsulfatase B (ARSB), iduronidase, α-glucosidase, and imiglucerase.

25. The method of claim 23, wherein the enzyme is selected from the group consisting of α-galactosidase A, arylsulfatase B (ARSB), iduronidase, α-glucosidase, and imiglucerase.

* * * * *